United States Patent [19]
Lanza et al.

[11] Patent Number: 6,126,936
[45] Date of Patent: *Oct. 3, 2000

[54] MICROCAPSULES AND COMPOSITE MICROREACTORS FOR IMMUNOISOLATION OF CELLS

[75] Inventors: Robert P. Lanza, Clinton; Willem M. Kühtreiber, Shrewsbury; William L. Chick, Wellesley, all of Mass.

[73] Assignee: BioHybrid Technologies LLC, Shrewsbury, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/402,209

[22] Filed: Mar. 10, 1995

[51] Int. Cl.$^7$ ........................... A61K 35/12; C12N 11/10; C12N 11/04; C12N 5/00
[52] U.S. Cl. ................... 424/93.7; 424/423; 435/177; 435/178; 435/182; 435/382; 435/395; 435/397
[58] Field of Search .................... 435/174, 177, 435/178, 180, 182, 240.2, 240.23, 382, 395, 397; 424/93.7

[56] References Cited

U.S. PATENT DOCUMENTS

| | | | |
|---|---|---|---|
| 4,353,888 | 10/1982 | Sefton | 424/25 |
| 4,391,909 | 7/1983 | Lim | 435/178 |
| 4,532,123 | 7/1985 | Gardner | 424/21 |
| 4,744,933 | 5/1988 | Rha et al. | 264/4.3 |
| 4,806,355 | 2/1989 | Goosen et al. | 424/424 |
| 5,084,350 | 1/1992 | Chang et al. | 428/402.2 |
| 5,227,298 | 7/1993 | Weber et al. | 435/178 |
| 5,459,054 | 10/1995 | Skjak-Braek et al. | 435/178 |

FOREIGN PATENT DOCUMENTS

| | | |
|---|---|---|
| 2024196 | 8/1990 | Canada . |
| 127 713 | of 1983 | European Pat. Off. . |
| 0 127 989 | of 1984 | European Pat. Off. . |
| 0180309A2 | of 1986 | European Pat. Off. . |
| 301 777 | of 1988 | European Pat. Off. . |
| 58-357725 | 3/1983 | Japan . |
| 125 7178 | 12/1968 | United Kingdom . |
| 123 6885 | 9/1969 | United Kingdom . |
| 2119734A | 3/1980 | United Kingdom . |
| WO83/03061 | 3/1983 | WIPO . |
| WO92/19195 | 4/1992 | WIPO . |
| WO94/15589 | 12/1992 | WIPO . |
| WO93/24112 | 5/1993 | WIPO . |
| WO94/12161 | 11/1993 | WIPO . |
| WO95/19743 | 7/1995 | WIPO . |

OTHER PUBLICATIONS

Chang, T.M.S. (1992) "Artificial Cells In Immobilization Biotechnology" *Biomat., Art. Cells & Immob. Biotech.* 20(5): 1121–1143.
Chang, T.M.S. (1980) "Artificial Cells: The Use of Hybrid Systems" *Artificial Organs* 4(4): 264–271.
Chang, T.M.S. (1993) "Bioencapsulation In Biotechnology" *Biomat., Art. Cells & Immob. Biotech.* 20(3): 291–297.
Chang, T.M.S. (1992) "Blood Substitutes Based On Modified Hemoglobin Prepared By Encapsulation Or Crosslinking: An Overview" *Biomat., Art. Cells & Immob. Biotech.* 20(2–40): 159–179.
Chang, T.M.S. (1993) "Living Cells and Microorganisms Immobilized By Microencapsulation Inside Artificial Cells" in *Fundamentals of Animal Cell Encapsulation and Immobilization* by Mattheus F.A. Goosen (London: CRC Press) 183–196.

(List continued on next page.)

*Primary Examiner*—David M. Naff

[57] ABSTRACT

Microcapsules and composite microreactors are prepared that immunoisolate living cells such as islet cells or genetically engineered cells. A reduced volume microcapsule is formed by coating a gel matrix particle with a polyamino acid of 15,000 daltons or less molecular weight to reduce volume of the particle by at least 30% as compared to volume prior to coating. A composite microreactor includes the microcapsule containing cell embedded in a gel matrix and provides a molecular weight cutoff that prevents molecules larger than about 400,000 daltons from containing the living cell. A double composite microreactor includes an internal particle that includes an internal particle gel matrix containing a living cell and having a coating, a particle that includes the internal particle embedded in a particle gel matrix and a coating, and a gel super matrix in which the particle is embedded. At least one of the coatings is a volume reducing coating of polyamino acid of 15,000 daltons or less molecular weight. The gel matrices may be alginate, the polyamino acid may be polylysine or polyornithine, and at least one of the gel matrices or coatings may be treated by aging for between 2 hours and 14 days. The internal particle, particle and composite microreactor may have diameters respectively between 50 and 700 microns, 400 and 800 microns and 300 and 1500 microns. to be implanted so there is little or no need for immunosuppressant or antifibrotic drugs. A reduced volume microcapsule is formed by coating a gel matrix particle with a polyamino acid of 15,000 daltons or less molecular weight to reduce volume of the particle by at least 30% as compared to volume prior to coating. A composite microreactor is provided by embedding the microcapsule when containing a living cell in a gel matrix to obtain a molecular weight cutoff that prevents molecules larger than about 400,000 daltons from contacting the living cell. A double composite microreactor is formed containing an internal particle including an internal particle gel matrix containing a living cell and having a coating, a particle including the internal particle embedded in a particle gel matrix having a coating, and a gel super matrix in which the particle is embedded. At least one of the coatings is a volume reducing coating of polyamino acid of 15,000 daltons or less molecular weight. The gel matrices may be alginate, the polyamino acid may be polylysine or polyornithine, and at least one of the gel matrices or coatings may be treated by aging for between 2 hours and 14 days. The internal particle, particle and composite microreactor may have diameters respectively between 50 and 700 microns, 400 and 800 microns and 300 and 1500 microns.

82 Claims, 1 Drawing Sheet

OTHER PUBLICATIONS

Chang, T.M.S. (1965) "Semipermeable Aqueous Microcapsules" Ph.D. Thesis (Montreal: McGill University, Department of Physiology).

Chang, T.M.S. et al., (1966) "Semipermeable Aqueous Microcapsules" *Canadian Journal of Physiology and Pharmacology* 44: 115–128.

Goosen (1987) "Insulin Delivery Systems and the Encapsulation of Cells for Medical and Industrial Use" *CRC Critical Reviews in Biocompatibility* 3(1): 1–24.

Goosen et al. (1985) "Immobilization of Living Cells in Biocompatible Semipermeable Microcapsule Biomedical and Potential Biochemical Engineering Applications" in *Polymers in Medicine II; Biomedical and Pharmaceutical Applications* Chiellini et al. (eds.) (NY: Plenum Press) 235–246.

Soon–Shiong, P. et al. (1991) "An Immunologic Basis for the Fibrotic Reaction to Implanted Microencapsules" *Transplantation Proceedings* 23(1): 758–759.

Soon–Shiong, P. et al. (1992) "Successful Reversal Of Spontaneous Diabetes In Dogs By Intraperitoneal Microencapsulated Islets" *Transplantation* 54(5): 769–774.

Sun et al. (1987) "Microencapsulated Cells As Hormone Delivery Systems" *CRC Critical Reviews in Therapeutic Drug Carrier Systems* 4(1): 1–12.

Wong, H. and T.M.S. Chang (1991) "A Novel Two Step Procedure for Immobilizing Living Cells In Microcapsules for Improving Xenograft Survival" *Biomat., Art. Cells & Immob. Biotech.* 19(4): 687–697.

Wong, H. et al. (1991) "The Microencapsulation Of Cells Within Alginate Poly–L–Lysine Microencapsules Prepared With The Standard Single Step Drop Technique: Histologically Identified Membrane Imperfections And The Associated Graft Rejection" *Biomat., Art. Cells & Immob. Biotech.* 19(4):675–686.

Dupuy et al., "Microencapsulation of isolated pituitary cells by polyacrylamide microlatex coagulation on agarose beads" Biomaterials 12:493–496 (1991).

Ito et al., "In vitro study of multicellular hapatocyte spheroids formed in microcapsules", Artif. Organs 16:422–427 (1992).

Leung et al., "Microencapsulation of crystalline insulin or islets of Langerhans: an insulin diffusion study", Artificial Organs 7:208–212 (1983).

Young, "Inverted Microcarriers: Using Microencapsulation to Grow Anchorage–Dependent Cells", *Fundamentals of Animal Cell Encapsulat5ion and Immobiliation, Goosen, Chapter II*, 1993.

Young et al., "Inverted Microcarriers: using microencapsulation to grow anchorage–dependent cells in suspension", BioPharm Nov./Dec. 1989.

MICROCAPSULES AND COMPOSITE MICROREACTORS FOR IMMUNOISOLATION OF CELLS

BACKGROUND OF THE INVENTION

The invention relates to gel particles such as beads or spheres and methods of their manufacture and use.

Transplantation of donor tissue into a recipient can be used to treat a wide variety of disorders, including heart disease, neoplastic disease, and endocrine disease. The clinical application of transplantation-based therapies is, however, limited by several factors. These factors include immune rejection of transplanted allogeneic or xenogeneic tissue by the transplant recipient, a shortage of allogeneic donor-tissue, and donor-propagated immune attack of recipient tissue (graft-versus-host-disease).

Immune rejection of transplanted donor-tissue may be the most serious barrier to more widespread availability of the benefits of transplantation-based therapies. Implantation of allogeneic or xenogeneic donor-tissue into an immunocompetent recipient generally results in a vigorous and destructive immune response directed against the donor-graft. Efforts to prevent immune-based destruction of donor tissue have generally fallen into two categories. In one approach, efforts have been directed to moderating the recipient's immune response, e.g., by the induction of specific immunological tolerance to transplanted tissue, or much more frequently, by the administration of broad-spectrum immune suppressants, e.g., cyclosporin. In the other major approach, efforts to prolong the acceptance of a donor-graft have been directed to rendering the donor-graft less susceptible to attack, e.g., by immunoisolating the donor-tissue by encapsulating it in a way which minimizes contact of elements of the recipient's immune system with the encapsulated donor tissue.

Immunoisolation is particularly attractive for the treatment of endocrine disorders or in hormone or enzyme replacement therapies. For example, the implantation of immunoisolated pancreatic islet cells can be used to restore glucose-responsive insulin function in a diabetic recipient. Islets can be placed in a mechanical enclosure, or can be coated with a material, which allows relatively free diffusion of glucose, insulin, nutrients, and cellular waste products but which is impervious to components of the recipient's immune system.

A microcapsule typically includes an inner core in which living cells are embedded and optionally an outer semipermeable coating. The outer coating often has a porosity which prevents components of the implant recipient's immune system from entering and destroying the cells within the microcapsule. Gel microcapsules containing a small number of living cells have been used to transplant both allogeneic and xenogeneic donor cells into recipient animals. Several methods for microencapsulating cells, e.g., pancreatic islet cells, in an alginate gel have been investigated. These include the alginate-polylysine technique described in Lim et al., U.S. Pat. No. 4,391,909 and Soon-Shiong et al., *Transplantation*, 54:769-774 (1992), the alginate-chitosan system described in Rha et al., U.S. Pat. No. 4,744,933, and the polyacrylate encapsulation method described in Sefton, U.S. Pat. No. 4,353,888.

SUMMARY OF THE INVENTION

The inventors have discovered that composite microreactors can be used to immunoisolate donor cells. Composite microreactors of the invention allow donor cells, e.g., porcine, bovine, canine, or human islet cells to be successfully transplanted into a recipient animal, e.g., mouse, rat, dog, or human with little or no need for immunosuppressant or antifibrotic drugs.

Accordingly, in one aspect, the invention features, a composite microreactor which includes:
(a) one, or a plurality, of an internal particle which includes:
    (i) a source of a therapeutic substance, e.g., an islet;
    (ii) an internal particle matrix, e.g., a gel core or a solid particle, which contacts the source;
    (iii) (optionally) an internal particle coating enclosing the internal particle matrix; and
(b) a super matrix, e.g., a gel super matrix, in which the internal particle (or particles) is embedded; and
(c) (optionally) an outer coating enclosing the super matrix, the composite microreactor preferably providing a molecular weight cutoff that prevents molecules larger than about 400,000 daltons from coming into contact with the source and wherein a component of the composite microereactor, e.g., the internal particle, the super matrix, or both, are geometrically stabilized.

In preferred embodiments the internal particle matrix is or includes: a gel, e.g., a hydrogel, e.g., an alginate or agarose gel; a solid particle, e.g., a glass bead; a particle having pores or interstices. In preferred embodiments the internal particle matrix is other than a liquid. The internal particle matrix can include substances which impede the passage of recipient-derived molecules or cells, e.g., it can include polyethylene oxide (PEO), polystyrene sulfonic acid (PSA), or polyornithine (PLO).

In preferred embodiments the internal particle matrix hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement.

In preferred embodiments the internal particle coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa, about 1 kDa-less than 4 kDa, e.g., 3.7 kDa, or about 5 kDa to less than about 15 kDa, or about 5 kDa to less than about 10 kDa, e.g., 9 kDa–10 kDa, e.g., 9.7 kDa. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix is or includes: a gel, e.g., a hydrogel, e.g., an alginate or agarose gel. In preferred embodiments the super matrix is other than a liquid. The super matrix can include substances which impede the passage of recipientderived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the super matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the outer coating (which is optional) is or includes: a polyaminoacid, e.g., polylysine (PLL) or PLO; a naturally occurring substance, e.g., chitosan. A particularly preferred coating is polyamino acid, e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa.

In preferred embodiments the outer coating hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the internal particle, before application of a volume-reducing coating, is between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the diameter of the composite microreactor is between 100 microns and 4 millimeters, between 300 and 1200 microns, between 300 and 1500 microns, between 400 and 1000 microns, or between 400 and 800 microns. More preferably the diameter is about 600 microns.

In preferred embodiments the composite microreactor includes a plurality of internal particles, e.g., between 2 and 100, e.g., 2 and 10, internal particles.

In preferred embodiments the composite microreactor is a component of a higher order composite, e.g., a double composite, or a third order composite.

In preferred embodiments one or more components of the composite is geometrically stabilized. For example: the internal particle matrix is geometrically stabilized, e.g., by allowing it to age for between 2 hours and 14 days, e.g., for between 12 hours and 4 or 5 days, prior to coating it; the internal particle is geometrically stabilized, e.g., by allowing it to age for between 2 hours and 14 days, e.g., for between 12 hours and 4 or 5 days prior to embedding it in the super matrix In preferred embodiments the internal particle coating has a lower molecular weight exclusion number than does the super matrix, the outer coating (if present), or the combination of the super matrix and the outer coating, e.g., the internal particle coating excludes recipient immune molecules, e.g., IgG or complement, and the super matrix, the outer coating (if present), or the combination of the super matrix and the outer coating, allows immune molecules, e.g., IgG or complement, to pass but excludes the passage of recipient cells.

In preferred embodiments the outer surface of the composite is biologically compatible, e.g., it is sufficiently smooth that it inhibits fibrotic encapsulation of the composite, but the surface of the internal particle is not biologically compatible, e.g., it is not sufficiently smooth to inhibit fibrotic encapsulation.

In preferred embodiments: at least one of the super matrix and the outer coating prevents contact of fibrotic cells with the internal particle coating.

In preferred embodiments the composite microreactor further includes:

(b) one, or a plurality, of a second internal particle which includes:

(i) a second source of a therapeutic substance, e.g., an islet or a cell other than an islet;

(ii) a second internal particle matrix which includes the second source, (iii) (optionally) a second internal particle coating enclosing the second internal particle;

In preferred embodiments: the super matrix prevents contact of fibrotic cells with the internal particle coating; the super matrix and the outer coating (if present) is free of defects which arise from the inclusion of non-geometrically stabilized components, e.g., non-geometrically stabilized internal particles; at least two, or three, or four, components chosen from the group of the internal particle matrix, the internal particle coating, the super matrix, and the outer coating (if present), provides a molecular weight cutoff that prevents molecules larger than about 150,000 daltons from coming into contact with the sources; the internal particle molecular weight cutoff is provided by a pore structure of the internal particle matrix, and that pore structure results, e.g., from cross-linking of the internal particle gel; the molecular weight cutoff of the super matrix is provided by a pore structure of the super matrix.

Preferred embodiments lack an outer coating.

In preferred embodiments the outer surface of the composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the outer component of the composite microreactor, i.e., the component in contact with the recipient, is at least 50, 75, 90, 95, 97, or 98%, water.

In preferred embodiments one or more components of the composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%; sufficient such that the concentration of small molecules (e.g., molecules which are not excluded by the semipermeable barrier-components of the composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments one or more components of the composite microreactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in or exclusion by the component or components which supply the separation), e.g., reduced by at least 10, 20, 50, 75, or 90%; sufficient to inhibit acute release of donor antigens. In more preferred embodiments: the distance or separation is supplied by one or both of the particle matrix and the super matrix.

In another aspect, the invention features, a composite microreactor which includes:

(a) one, or a plurality, of an internal particle which includes:
  (i) a source of a therapeutic substance, e.g., an islet;
  (ii) an internal particle matrix which contacts the first source; and
  (iii) an internal particle coating of a polyamino acid enclosing the internal particle matrix.
(b) a super matrix in which the internal particle (or particles) is embedded;
(c) (optionally) an outer coating enclosing the super matrix, the composite microreactor preferably providing a molecular weight cutoff that prevents molecules larger than about 400,000 daltons from coming into contact with the source.

In preferred embodiments the internal particle matrix is or includes: a gel, e.g., a hydrogel, e.g., an alginate or agarose gel; a solid particle, e.g., a glass bead; a particle having pores or interstices. In preferred embodiments the internal particle matrix is other than a liquid. The internal particle matrix can include substances which impede the passage of recipient-derived molecules or cells, e.g., it can include polyethylene oxide (PEO), polystyrene sulfonic acid (PSA), or polyornithine (PLO).

In preferred embodiments the internal particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the internal particle coating is or includes: a polyaminoacid, e.g., polylysine (PLL) or PLO. A particularly preferred coating is a polyamino acid, e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix is or includes: a gel, e.g., a hydrogel, e.g., an alginate or agarose gel. In preferred embodiments the super matrix is other than a liquid. The super matrix can include substances which impede the passage of recipientderived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the super matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the outer coating (which is optional) is or includes: a polyaminoacid, e.g., polylysine (PLL) or PLO; a naturally occurring substance, e.g., chitosan. A particularly preferred coating is polyamino acid, e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa.

In preferred embodiments the outer coating hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the internal particle, before application of a volume-reducing coating, is between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the diameter of the composite microreactor is between 100 microns and 4 millimeters, between 300 and 1200 microns, between 300 and 1500 microns, between 400 and 1000 microns, or between 400 and 800 microns. More preferably the diameter is about 600 microns.

In preferred embodiments the composite microreactor includes a plurality of internal particles, e.g., between 2 and 100, e.g., 2 and 10, internal particles.

In preferred embodiments the composite microreactor is a component of a higher order composite, e.g., a double composite, or a third order composite.

In preferred embodiments one or more components of the composite is geometrically stabilized. For example: the first internal particle matrix is geometrically stabilized, e.g., by allowing it to age for between 2 hours and 14 days, e.g., for between 12 hours and 4 or 5 days, prior to coating it; the first internal particle is geometrically stabilized, e.g., by allowing it to age for between 2 hours and 14 days, e.g., for between 12 hours and 4 or 5 days prior to embedding it in the super matrix.

In preferred embodiments the internal particle coating has a lower molecular weight exclusion number than does the super matrix, the outer coating (if present), or the combination of the super matrix and the outer coating, e.g., the internal particle coating excludes recipient immune molecules, e.g., IgG or complement, and the super matrix, the outer coating (if present), or the combination of the super matrix and the outer coating, allows immune molecules, e.g., IgG, or complement, to pass but excludes the passage of recipient cells.

In preferred embodiments: the outer surface of the composite is biologically compatible, e.g., it is sufficiently smooth that it inhibits fibrotic encapsulation of the composite; the outer surface of the composite is biologically compatible, e.g., it is sufficiently smooth that it inhibit fibrotic encapsulation of the composite but the surface of the internal particle is not biologically compatible, e.g., it is not sufficiently smooth to inhibit fibrotic encapsulation.

In preferred embodiments: at least one of the super matrix and the outer coating prevent contact of fibrotic cells with the internal particle coating.

In preferred embodiments the composite microreactor further includes:

one, or a plurality, of a second internal particle which includes:

(i) a second source of a therapeutic substance, (ii) a second internal particle matrix which includes the second source, (iii) a second internal particle coating enclosing the second internal particle matrix, the second internal particle being embedded in the super matrix.

In preferred embodiments: the super matrix prevents contact of fibrotic cells with the internal particle coating; the super matrix and the outer coating (if present) are free of defects which arise from the inclusion of non-geometrically stabilized components, e.g., non-geometrically stabilized internal particles; at least two, or three, or four, components chosen from the group of the internal particle matrix, the internal particle coating, the super matrix, and the outer coating (if present), provides a molecular weight cutoff that prevents molecules larger than about 150,000 daltons from coming into contact with the sources; the internal particle molecular weight cutoff is provided by a pore structure of the internal particle matrix, and that pore structure results, e.g., from cross-linking of the internal particle gel; the molecular weight cutoff of the super matrix is provided by a pore structure of the super matrix.

Preferred embodiments lack an outer coating.

In preferred embodiments the outer surface of the composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the outer component of the composite microreactor, i.e., the component in contact with the recipient, is at least 50, 75, 90, 95, 97, or 98%, water.

In preferred embodiments one or more components of the composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%; sufficient such that the concentration of small molecules (e.g., molecules which are not excluded by the semipermeable barrier-components of the composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments one or more components of the composite microreactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in or exclusion by the component or components which supply the separation), e.g., reduced by at least 10, 20, 50, 75, or 90%; sufficient to inhibit acute release of donor antigens. In more preferred embodiments: the distance or separation is supplied by one or both of the particle matrix and the super matrix.

In another aspect, the invention features, a composite microreactor which includes:

(a) one, or a plurality, of an internal particle which includes:
 (i) a source of a therapeutic substance, e.g., an islet;
 (ii) an internal particle matrix which contacts the source; and
 (iii) an internal particle coating enclosing the internal particle matrix;
(b) a (non-liquid) gel super matrix in which the internal particle (or particles) is embedded;
(c) (optionally) an outer coating enclosing the super matrix, the composite microreactor preferably providing a molecular weight cutoff that prevents molecules larger than about 400,000 daltons from coming into contact with the sources.

In preferred embodiments the internal particle matrix is or includes: a gel, e.g., a hydrogel, e.g., an alginate or agarose gel; a solid particle, e.g., a glass bead; a particle having pores or interstices. In preferred embodiments the internal particle matrix is other than a liquid. The internal particle matrix can include substances which impede the passage of recipient-derived molecules or cells, e.g., it can include polyethylene oxide (PEO), polystyrene sulfonic acid (PSA), or polyornithine (PLO).

In preferred embodiments the internal particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the internal particle coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa, about 1 kDa-less than 4 kDa. e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix is or includes: a gel, e.g., a hydrogel, e.g., an alginate or agarose gel. The super matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the super matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the outer coating (which is optional) is or includes: a polyaminoacid, e.g., polylysine (PILL) or PLO; a naturally occurring substance, e.g., chitosan. A particularly preferred coating is a polyamino acid, e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa.

In preferred embodiments the outer coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the internal particle, before application of a volume-reducing coating, is between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the diameter of the composite microreactor is between 100 microns and 4 millimeters, between 300 and 1200 microns, between 300 and 1500 microns, between 400 and 1000 microns, or between 400 and 800 microns. More preferably the diameter is about 600 microns.

In preferred embodiments the composite microreactor includes a plurality of internal particles, e.g., between 2 and 100, e.g., 2 and 10, internal particles.

In preferred embodiments the composite microreactor is a component of a higher order composite, e.g., a double composite, or a third order composite.

In preferred embodiment one or more components of the composite is geometrically stabilized. For example: the first internal particle matrix is geometrically stabilized, e.g., by allowing it to age for between 2 hours and 14 days, e.g., for between 12 hours and 4 or 5 days, prior to coating it; the first internal particle is geometrically stabilized, e.g., by allowing it to age for between 2 hours and 14 days, e.g., for between 12 hours and 4 or 5 days prior to embedding it in the super matrix In preferred embodiments the internal particle coating has a lower molecular weight exclusion number than does the super matrix, the outer coating (if present), or the combination of the super matrix and the outer coating, e.g., the internal particle coating excludes recipient immune molecules, e.g., IgG or complement, and the super matrix, the outer coating (if present), or the combination of the super matrix and the outer coating, allows immune molecules, e.g., IgG, or complement, to pass but excludes the passage of recipient cells.

In preferred embodiments: the outer surface of the composite is biologically compatible, e.g., it is sufficiently smooth that it inhibits fibrotic encapsulation of the composite, but the surface of the internal particle is not biologically compatible, e.g., it is not sufficiently smooth to inhibit fibrotic encapsulation.

In preferred embodiments: at least one of the super matrix and the outer coating prevent contact of fibrotic cells with the internal particle coating.

In preferred embodiments the composite microreactor further includes:

one, or a plurality, of a second internal particle comprising:
(i) a second source of a therapeutic substance,
(ii) a second internal particle matrix which includes the second source,
(iii) (optionally) a second internal particle coating enclosing the second internal particle matrix, the second internal particle being embedded in the super matrix.

In preferred embodiments: the super matrix prevents contact of fibrotic cells with the internal particle coating; the super matrix and the outer coating (if present) is free of defects which arise from the inclusion of non-geometrically stabilized components, e.g., non-geometrically stabilized internal particles; at least two, or three, or four, components chosen from the group of the internal particle matrix, the internal particle coating, the super matrix, and the outer coating (if present), provides a molecular weight cutoff that prevents molecules larger than about 150,000 daltons from coming into contact with the sources; the internal particle molecular weight cutoff is provided by a pore structure of the internal particle matrix, and that pore structure results, e.g., from cross-linking of the internal particle gel; the molecular weight cutoff the super matrix is provided by a pore structure of the super matrix.

Preferred embodiments lack an outer coating.

In preferred embodiments the outer surface of the composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the outer component of the composite microreactor, i.e., the component in contact with the recipient, is at least 50, 75, 90, 95, 97, or 98%, water.

In preferred embodiments one or more components of the composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%; sufficient such that the concentration of small molecules (e.g., molecules which are not excluded by the semipermeable barrier-components of the composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments one or more components of the composite microreactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in or exclusion by the component or components which supply the separation), e.g., reduced by at least 10, 20, 50, 75, or 90%; sufficient to inhibit acute release of donor antigens. In more preferred embodiments: the distance or separation is supplied by one or both of the particle matrix and the super matrix.

In another aspect, the invention features, a composite microreactor which includes:

(a) one, or a plurality, of a geometrically stabilized internal particle which includes:
(i) an islet,
(ii) an internal particle gel matrix in which the islet is embedded,
(iii) an internal particle coating of polylysine enclosing the internal particle matrix; and
(b) a gel super matrix in which the internal particle (or particles) is embedded, the composite microreactor providing a molecular weight cutoff that prevents molecules larger than about 400,000 daltons from coming into contact with the sources.

In preferred embodiments the internal particle gel matrix is or includes: a hydrogel, e.g., an alginate or agarose gel. In preferred embodiments the internal particle matrix is other than a liquid. The internal particle matrix can include substances which impede the passage of recipient-derived molecules or cells, e.g., it can include polyethylene oxide (PEO), polystyrene sulfonic acid (PSA), or polyornithine (PLO).

In preferred embodiments the internal particle coating is or includes: a polylysine (PLL) having a molecular weight of less than 15 kDa, more preferably of less than 10 kDa, more preferably of less than 5 kDa. Particularly preferred are polylysines with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the gel super matrix is or includes: a hydrogel, e.g., an alginate or agarose gel. In preferred embodiments the super matrix is other than a liquid. The super matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the super matrix hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the diameter of the internal particle, before application of a volume-reducing coating, is between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the diameter of the composite microreactor is between 100 microns and 4 millimeters, between 300 and 1200 microns, between 300 and 1500 microns, between 400 and 1000 microns, or between 400 and 800 microns. More preferably the diameter is about 600 microns.

In preferred embodiments the composite microreactor includes a plurality of internal particles, e.g., between 2 and 100, e.g., 2 and 10, internal particles.

In preferred embodiments the composite microreactor is a component of a higher order composite, e.g., a double composite, or a third order composite.

In preferred embodiments one or more components of the composite is geometrically stabilized. For example: the first internal particle matrix is geometrically stabilized, e.g., by allowing it to age for between 2 hours and 14 days, e.g., for between 12 hours and 4 or 5 days, prior to coating it; the first internal particle is geometrically stabilized, e.g., by allowing it to age for between 2 hours and 14 days, e.g., for between 12 hours and 4 or 5 days prior to embedding it in the super matrix In preferred embodiments the internal particle coating has a lower molecular weight exclusion number than does the super matrix; the internal particle coating excludes recipient immune molecules, e.g., IgG or complement, and the super matrix allows immune molecules, e.g., IgG, or complement, to pass but excludes the passage of recipient cells.

In preferred embodiments: the outer surface of the composite is biologically compatible, e.g., it is sufficiently smooth that it inhibits fibrotic encapsulation of the composite, but the surface of the internal particle is not biologically compatible, e.g., it is not sufficiently smooth to inhibit fibrotic encapsulation.

In preferred embodiments: at least one of the super matrix and the outer coating prevent contact of fibrotic cells with the internal particle coating.

In preferred embodiments: super matrix prevents contact of fibrotic cells with the internal particle coating; the super matrix and the outer coating (if present) is free of defects which arise from the inclusion of non-geometrically stabilized components, e.g., non-geometrically stabilized internal particles; at least two, or three, or four, components chosen from the group of the internal particle matrix, the internal particle coating, the super matrix, and the outer coating (if present), provides a molecular weight cutoff that prevents molecules larger than about 150,000 daltons from coming into contact with the sources; the internal particle molecular weight cutoff is provided by a pore structure of the internal particle matrix, and that pore structure results, e.g., from cross-linking of the internal particle gel; the molecular weight cutoff the super matrix is provided by a pore structure of the super matrix.

Preferred embodiments lack an outer coating.

In preferred embodiments the outer surface of the composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the outer component of the composite microreactor, i.e., the component in contact with the recipient, is at least 50, 75, 90, 95, 97, or 98%, water.

In preferred embodiments one or more components of the composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%;

sufficient such that the concentration of small molecules (e.g., molecules which are not excluded by the semipermeable barrier-components of the composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments one or more components of the composite micro reactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in or exclusion by the component or components which supply the separation), e.g., reduced by at least 10, 20, 50, 75, or 90%; sufficient to inhibit acute release of donor antigens. In more preferred embodiments: the distance or separation is supplied by one or both of the particle matrix and the super matrix.

The inventors have discovered that a single or simple composite microreactor, e.g., one which includes one or more microcapsules contained in a larger particle, can be used to immunoisolate donor tissue. They have further discovered that higher order composites, e.g., double composites, which include one or more single composites contained in a larger particle, are also effective for immunoisolating donor tissue.

Accordingly, the invention features, a double composite microreactor which includes:

(1) one, or a plurality, of an internal particle which includes:
  (a) a source of a therapeutic substance, e.g., an islet;
  (b) an internal particle matrix which contacts the source; and
  (c) (optionally) an internal particle coating enclosing the first internal particle matrix;
(2) one, or a plurality, of a particle which includes:
  (a) the internal particle or particles of (1)
  (b) a particle matrix in which the internal particle (or internal particles) is embedded; and
  (c) (optionally) a particle coating enclosing the particle;
(3) a super matrix in which the particle (or particles) of (2) is embedded; and
(4) (optionally) a super matrix or outer coating, e.g., of polylysine enclosing the super matrix.

In preferred embodiments the internal particle matrix is or includes: a gel, e.g., a hydrogel, e.g., an alginate or agarose gel; a solid particle, e.g., a glass bead; a particle having pores or interstices. In preferred embodiments the internal particle matrix is other than a liquid. The internal particle matrix can include substances which impede the passage of recipient-derived molecules or cells, e.g., it can include polyethylene oxide (PEO), polystyrene sulfonic acid (PSA), or polyornithine (PLO).

In preferred embodiments the internal particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the internal particle coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa, about 1 kDa-less than 4 kDa. e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the internal particle, before application of a volume-reducing coating, between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the particle matrix is or includes: a gel, e.g., a hydrogel, e.g., an alginate or agarose gel. In preferred embodiments the particle matrix is other than a liquid. The particle matrix can include substances which impede the passage of recipient-derived molecules or cells, e.g., it can include polyethylene oxide (PEO), polystyrene sulfonic acid (PSA), or polyornithine (PLO).

In preferred embodiments the particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the particle coating is or includes: a polyaminoacid, e.g., polylysine (PILL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the particle, before application of a volume-reducing coating, is between 200 and 1,000 microns, more preferably between 400 and 800 microns, more preferably between 500 and 700 microns, and most preferably about 600 microns in diameter. The diameter of the particles, after application of a volume-reducing coating, is preferably between 100 and 700 microns, more preferably between 250 and 550 microns, more preferably between 300 and 500 microns, and most preferably about 400 microns in diameter.

In preferred embodiments the super matrix has little or no ability to exclude low molecular weight species, e.g., IgG or complement, with this property being relegated to other components of the microcapsule.

In preferred embodiments the gel super matrix is or includes: a hydrogel, e.g., an alginate or agarose gel. In preferred embodiments the super matrix is other than a liquid. The super matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the super matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the super matrix coating (which is optional) is or includes: a polyaminoacid, e.g., polylysine (PLL) or PLO; a naturally occurring substance, e.g., chitosan. Particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa.

In preferred embodiments the particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the double composite microreactor is, before application of a volume-reducing coating, between 400 and 1,500 microns, more preferably between 500 and 1,300 microns, more preferably between 600 and 1,100 microns, and most preferably about 900 microns in diameter. The diameter of the double composite microreactor is, after application of a volume-reducing coating, is preferably between 300 and 1,300 microns, more preferably between 400 and 1,200 microns, more preferably between 500 and 1,000 microns, and most preferably about 800 microns in diameter.

In preferred embodiments the composite microreactor includes a plurality of internal particles, e.g., between 2 and 100, e.g., between 2 and 10, internal particles.

In preferred embodiments the composite microreactor includes a plurality of particles, e.g., between 2 and 100, e.g., 2 and 10, particles.

In preferred embodiments the double composite microreactor is a component of a higher order composite, e.g., a third or fourth order composite.

In preferred embodiment one or more components of the composite is geometrically stabilized. For example: the first internal particle matrix is geometrically stabilized, e.g., by allowing it to age for between 2 hours and 14 days, e.g., for between 12 hours and 4 or 5 days, prior to coating it; the first internal particle is geometrically stabilized, e.g., by allowing it to age for between 2 hours and 14 days, e.g., for between 12 hours and 4 or 5 days prior to embedding it in the particle matrix; the first particle matrix is geometrically stabilized, e.g., by allowing it to age for between 2 hours and 14 days, e.g., for between 12 hours and 4 or 5 days, prior to coating it; the first particle is geometrically stabilized, e.g., by allowing it to age for between 2 hours and 14 days, e.g., for between 12 hours and 4 or 5 days prior to embedding it in the super matrix; the super matrix is geometrically stabilized, e.g., by allowing it to age for between 2 hours and 14 days, e.g., for between 12 hours and 4 or 5 days prior to coating it; the coated super matrix is geometrically stabilized, e.g., by allowing it to age for between 2 hours and 14 days, e.g., for between 12 hours and 4 or 5 days.

In preferred embodiments the internal particle coating has a lower molecular weight exclusion number than does the particle matrix, the super matrix, the outer coating (if present), or a combination of one or more of these, e.g., the internal particle coating excludes recipient immune molecules, e.g., IgG or complement, and the particle matrix, super matrix, the outer coating (if present), or a combination of these, allows immune molecules, e.g., IgG, or complement, to pass but excludes the passage of recipient cells.

In preferred embodiments the outer surface of the composite is biologically compatible, e.g., it is sufficiently smooth that it inhibits fibrotic encapsulation of the composite, but the surface of the internal particle (or of the particle) is not biologically compatible, e.g., it is not sufficiently smooth to inhibit fibrotic encapsulation.

In preferred embodiments: the first source is an islet; the second source is an islet; the third source is an islet; the fourth source is an islet; one source is an islet and another source is other than an islet, e.g. an erythrocyte, an acinar cell, or an adrenal cell.

In preferred embodiments an internal particle coating is a low molecular weight polyamino acid e.g., 1 kDa–4 kDa, about 1 kDa-less than 4 kDa and a particle coating is a low molecular weight polyamino acid e.g., 5 kDa to less than about 10 kDa, 5 kDa to less than about 15 kDa, e.g., about 9 kDa–10 kDa.

In preferred embodiments an internal particle coating has an exclusion limit of about 150 kDa and the first particle coating has an exclusion limit of about 400 kDa.

In preferred embodiments an internal particle coating has an exclusion limit of about 150 kDa and the particle matrix, first particle coating, super matrix, outer coating, or a combination thereof, has an exclusion limit of about 400 kDa.

In preferred embodiments an internal particle coating has an exclusion limit which is lower than that of the particle coating, e.g., the internal particle coating has an exclusion limit which will exclude molecules which are the size of IgG, or Clq, or larger, and the particle coating has an exclusion limit which, though permeable to IgG, or Clq, will exclude objects, e.g., cells, having a molecular weight of one million or more.

In preferred embodiments an internal particle coating has an exclusion limit which is lower than that of the particle coating, e.g., the internal particle coating has an exclusion limit which will exclude molecules which are the size of IgG, or Clq, or larger, and the particle matrix, first particle coating, super matrix, outer coating, or a combination thereof, has an exclusion limit which, though permeable to IgG, or Clq, will exclude objects, e.g., cells, having a molecular weight of one million or more.

In preferred embodiments there is a buffer-zone component, e.g., the particle matrix, which is disposed between a component which is not biocompatible, e.g., which is not anti fibrotic, e.g., the internal particle coating, and a component which has an exclusion limit which excludes the passage of recipient cells, e.g., the super matrix or outer coating.

In preferred embodiments: an internal particle coating has an exclusion limit which will exclude molecules which are the size of IgG, or Clq, or larger, the particle matrix is not free of defects which arise from the use of non-geometrically stabilized components, and the super matrix, outer coating, or a combination thereof, has an exclusion limit which, though permeable to IgG, or Clq, will exclude objects, e.g., cells, having a molecular weight of one million or more.

In preferred embodiments, the first particle of the double composite microreactor further includes:
one, or a plurality, of a second internal particle which includes:
 (i) a second source of a therapeutic substance, e.g., an islet;
 (ii) a second internal particle matrix which contacts the second source;
 (iii) a second internal particle coating enclosing the second internal particle matrix;

In preferred embodiments, the double composite microreactor further includes: one, or a plurality, of a second particle which includes:
(a) a third internal particle which includes:
 (i) a third source of a therapeutic substance, e.g., an islet,
 (ii) a third internal particle matrix which contacts the third source,
 (iii) (optionally) a third internal particle coating enclosing the third internal particle matrix; and
(b) (optionally) a fourth internal particle which includes:
 (i) a fourth source of a therapeutic substance, e.g., an islet,
 (ii) a fourth internal particle matrix which contacts the fourth source,
 (iii) a fourth internal particle coating enclosing the fourth internal particle matrix.

In preferred embodiments: one or more of the particle matrix, particle covering, or super matrix, prevents contact of fibrotic cells with the internal particle coating; the particle matrix, super matrix or the outer coating (if present) is free of defects which arise from the inclusion of non-geometrically stabilized components, e.g., non-geometrically stabilized internal particles; at least two, or three, or four, components chosen from the group of the particle matrix, the particle coating, the super matrix, and the outer coating (if present), provides a molecular weight cutoff that prevents molecules larger than about 150,000 daltons from coming into contact with the internal particle coating; the internal particle molecular weight cutoff is provided by a pore structure of the internal particle matrix, and that pore structure results, e.g., from cross-linking of the internal particle gel; the molecular weight cutoff the super matrix is provided by a pore structure of the super matrix.

Preferred embodiments lack an outer coating.

In preferred embodiments the outer surface of the double (or higher order) composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the internal particle coating is polylysine of about 5 kDa to less than about 15 kDa, or about 5 kDa to less than about 10 kDa, e.g., 9 kDa–10 kDa, and the particle coating is polylysine of about 5 kDa to less than about 15 kDa, or about 5 kDa to less than about 10 kDa, e.g., about 9 kDa–10 kDa.

In preferred embodiments the internal particle coating is polylysine of about 1 kDa–4 kDa (or about 1 kDa-less than 4 kDa) e.g.,about 2 kDa- 3 kDa, and the particle coating is polylysine of about 5 kDa to less than about 15 kDa, or about 5 kDa to less than about 10 kDa, e.g., about 9 kDa–10 kDa.

In preferred embodiments the internal particle coating is polylysine of about 1 kDa–4 kDa (or about 1 kDa-less than 4 kDa) e.g.,about 2 kDa- 3 kDa, and the particle coating is polylysine of about 1 kDa–4 kDa (or about 1 kDa-less than 4 kDa) e.g.,about 2 kDa- 3 kDa.

In preferred embodiments the outer component of the double composite microreactor, i.e., the component in contact with the recipient, is at least 50, 75, 90, 95, 97, or 98%, water.

In preferred embodiments one or more components of the double composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%;

sufficient such that the concentration of small molecules (e.g., molecules which are not excluded by the semipermeable barrier-components of the double composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments one or more components of the double composite microreactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in or exclusion by the component or components which supply the separation), e.g., reduced by at least 10, 20, 50, 75, or 90%; sufficient to inhibit acute release of donor antigens. In more preferred embodiments: the distance or separation is supplied by one or both of the particle matrix and the super matrix.

In yet another aspect, the invention features, a double composite microreactor which includes:

(1) one, or a plurality, of an internal particle which includes:
  (a) an islet;
  (b) an internal particle matrix of alginate in which the islet is embedded;
  (c) an internal particle coating of polylysine enclosing the first internal particle matrix;

(2) one, or a plurality of, a geometrically stabilized particle which includes:
  (a) the internal particle (or internal particles) of (1);
  (b) a particle matrix of alginate in which the internal particle (or internal particles) is embedded; and
  (c) a particle coating of polylysine enclosing the particle; and (3) a gel super matrix of agarose in which the particle (or particles) of (2) is embedded.

In preferred embodiments the internal particle coating is polylysine of about 5 kDa to less than about 15 kDa, or about 5 kDa to less than about 10 kDa, e.g., 9 kDa–10 kDa, and the particle coating is polylysine of about 5 kDa to less than about 15 kDa, or about 5 kDa to less than about 10 kDa, e.g., about 9 kDa–10 kDa.

In preferred embodiments the internal particle coating is polylysine of about 1 kDa–4 kDa (or about 1 kDa-less than 4 kDa) e.g.,about 2 kDa- 3 kDa, and the particle coating is polylysine of about 5 kDa to less than about 15 kDa, or about 5 kDa to less than about 10 kDa, e.g., about 9 kDa–10 kDa.

In preferred embodiments the internal particle coating is polylysine of about 1 kDa–4 kDa (or about 1 kDa-less than 4 kDa) e.g.,about 2 kDa- 3 kDa, and the particle coating is polylysine of about 1 kDa–4 kDa (or about 1 kDa-less than 4 kDa) e.g.,about 2 kDa- 3 kDa.

In preferred embodiments the internal particle coating is polylysine of about 5 kDa to less than about 15 kDa, or about 5 kDa to less than about 10 kDa, e.g., 9 kDa–10 kDa, and the particle coating is polylysine of about 1 kDa–4 kDa (or about 1 kDa-less than 4 kDa) e.g.,about 2 kDa- 3 kDa.

In preferred embodiments the internal particle matrix is other than a liquid. The internal particle matrix can include substances which impede the passage of recipient-derived molecules or cells, e.g., it can include polyethylene oxide (PEO), polystyrene sulfonic acid (PSA), or polyornithine (PLO).

In preferred embodiments the internal particle matrix hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the internal particle coating is or includes: a polylysine having a molecular weight of less than 15 kDa, more preferably of less than 10 kDa, more preferably of less than 5 kDa. Particularly preferred are polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the internal particle, before application of a volume-reducing coating, between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the particle matrix is other than a liquid. The particle matrix can include substances which impede the passage of recipient-derived molecules or cells, e.g., it can include polyethylene oxide (PEO), polystyrene sulfonic acid (PSA), or polyornithine (PLO).

In preferred embodiments the particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the particle coating is polylysine having a molecular weight of less than 15 kDa, more preferably of less than 10 kDa, more preferably of less than 5 kDa. Particularly preferred are polylysines with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the particle, before application of a volume-reducing coating, is between 200 and 1,000 microns, more preferably between 400 and 800 microns, more preferably between 500 and 700 microns, and most preferably about 600 microns in diameter. The diameter of the particles, after application of a volume-reducing coating, is preferably between 100 and 700 microns, more preferably between 250 and 550 microns, more preferably between 300 and 500 microns, and most preferably about 400 microns in diameter.

In preferred embodiments the super matrix has little or no ability to exclude low molecular weight species, e.g., IgG or complement, with this property being relegated to other components of the microcapsule.

In preferred embodiments the super matrix is other than a liquid. The super matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the super matrix hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the super matrix coating (which is optional) is or includes: a polyaminoacid, e.g., polylysine (PLL) or PLO; a naturally occurring substance, e.g., chitosan. Particularly preferred coating is polyamino acid. e.g., polylysine or polyornithine, having a molecular weight of less than 15 kDa, more preferably of less than 10 kDa, more preferably of less than 5 kDa. Particularly preferred are polylysines with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa.

In preferred embodiments the particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the double composite microreactor is, before application of a volume-reducing coating, between 400 and 1,500 microns, more preferably between 500 and 1,300 microns, more preferably between 600 and 1,100 microns, and most preferably about 900 microns in diameter. The diameter of the double composite microreactor is, after application of a volume-reducing coating, is preferably between 300 and 1,300 microns, more preferably between 400 and 1,200 microns, more preferably between 500 and 1,000 microns, and most preferably about 800 microns in diameter.

In preferred embodiments the composite microreactor includes a plurality of internal particles, e.g., between 2 and 100, e.g., between 2 and 10, internal particles.

In preferred embodiments the composite microreactor includes a plurality of particles, e.g., between 2 and 100, e.g., 2 and 10, particles.

In preferred embodiments the double composite microreactor is a component of a higher order composite, e.g., a third or fourth order composite.

In preferred embodiment one or more components of the composite is geometrically stabilized. For example: the first internal particle matrix is geometrically stabilized, e.g., by allowing it to age for between 2 hours and 14 days, e.g., for between 12 hours and 4 or 5 days, prior to coating it; the first internal particle is geometrically stabilized, e.g., by allowing it to age for between 2 hours and 14 days, e.g., for between 12 hours and 4 or 5 days prior to embedding it in the particle matrix; the first particle matrix is geometrically stabilized, e.g., by allowing it to age for between 2 hours and 14 days, e.g., for between 12 hours and 4 or 5 days, prior to coating it; the first particle is geometrically stabilized, e.g., by allowing it to age for between 2 hours and 14 days, e.g., for between 12 hours and 4 or 5 days prior to embedding it in the super matrix; the super matrix is geometrically stabilized, e.g., by allowing it to age for between 2 hours and 14 days, e.g., for between 12 hours and 4 or 5 days prior to coating it; the coated super matrix is geometrically stabilized, e.g., by allowing it to age for between 2 hours and 14 days, e.g., for between 12 hours and 4 or 5 days.

In preferred embodiments the internal particle coating has a lower molecular weight exclusion number than does the particle matrix, the super matrix, the outer coating (if present), or a combination of one or more of these, e.g., the internal particle coating excludes recipient immune molecules, e.g., IgG or complement, and the particle matrix, super matrix, the outer coating (if present), or a combination of these, allows immune molecules, e.g., IgG, or complement, to pass but excludes the passage of recipient cells.

In preferred embodiments the outer surface of the composite is biologically compatible, e.g., it is sufficiently smooth that it inhibits fibrotic encapsulation of the composite, but the surface of the internal particle (or of the particle) is not biologically compatible, e.g., it is not sufficiently smooth to inhibit fibrotic encapsulation.

In preferred embodiments: the first source is an islet; the second source is an islet; the third source is an islet; the fourth source is an islet; one source is an islet and another source is other than an islet, e.g. an erythrocyte, an acinar cell, or an adrenal cell.

In preferred embodiments an internal particle coating is a low molecular weight polyamino acid e.g., 1 kDa–4 kDa, about 1 kDa-less than 4 kDa and a particle coating is a low molecular weight polyamino acid e.g., 5 kDa to less than about 10 kDa, 5 kDa to less than about 15 kDa, e.g., about 9 kDa–10 kDa.

In preferred embodiments an internal particle coating has an exclusion limit of about 150 kDa and the first particle coating has an exclusion limit of about 400 kDa.

In preferred embodiments an internal particle coating has an exclusion limit of about 150 kDa and the particle matrix, first particle coating, super matrix, outer coating, or a combination thereof, has an exclusion limit of about 400 kDa.

In preferred embodiments an internal particle coating has an exclusion limit which is lower than that of the particle coating, e.g., the internal particle coating has an exclusion limit which will exclude molecules which are the size of IgG, or Clq, or larger, and the particle coating has an exclusion limit which, though permeable to IgG, or Clq, will exclude objects, e.g., cells, having a molecular weight of one million or more.

In preferred embodiments: an internal particle coating has an exclusion limit which is lower than that of the particle coating, e.g., the internal particle coating has an exclusion limit which will exclude molecules which are the size of IgG, or Clq, or larger, and the particle matrix, first particle coating, super matrix, outer coating, or a combination thereof, has an exclusion limit which, though permeable to IgG, or Clq, will exclude objects, e.g., cells, having a molecular weight of one million or more.

In preferred embodiments there is a buffer-zone component, e.g., the particle matrix, which is disposed between a component which is not biocompatible, e.g., which is not anti fibrotic, e.g., the internal particle coating, and a component which has an exclusion limit which excludes the passage of recipient cells, e.g., the super matrix or outer coating.

In preferred embodiments an internal particle coating has an exclusion limit which will exclude molecules which are the size of IgG, or Clq, or larger, the particle matrix is not free of defects which arise from the use of non-geometrically stabilized components, and the super matrix, outer coating, or a combination thereof, has an exclusion limit which, though permeable to IgG, or Clq, will exclude objects, e.g., cells, having a molecular weight of one million or more.

In preferred embodiments: one or more of the particle matrix, particle covering, or super matrix, prevents contact of fibrotic cells with the internal particle coating; the particle matrix, super matrix or the outer coating (if present) is free of defects which arise from the inclusion of non-geometrically stabilized components, e.g., non-geometrically stabilized internal particles; at least two, or three, or four, components chosen from the group of the particle matrix, the particle coating, the super matrix, and the outer coating (if present), provides a molecular weight cutoff that prevents molecules larger than about 150,000 daltons from coming into contact with the internal particle coating; the internal particle molecular weight cutoff is provided by a pore structure of the internal particle matrix, and that pore structure results, e.g., from cross-linking of the internal particle gel; the molecular weight cutoff the super matrix is provided by a pore structure of the super matrix.

Preferred embodiments lack an outer coating.

In preferred embodiments the outer surface of the composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the outer component of the double composite microreactor, i.e., the component in contact with the recipient, is at least 50, 75, 90, 95, 97, or 98%, water.

In preferred embodiments one or more components of the double composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%; sufficient such that the concentration of small molecules (e.g., molecules which are not excluded by the semipermeable barrier-components of the double composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments one or more components of the double composite microreactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in or exclusion by the component or components which supply the separation), e.g., reduced by at least 10, 20, 50, 75, or 90%; sufficient to inhibit acute release of donor antigens. In more preferred embodiments: the distance or separation is supplied by one or both of the particle matrix and the super matrix.

The inventors have also discovered a method of improving the performance of a microcapsule, e.g., a composite microreactor which includes "geometrically stabilizing" one or more components of the microcapsule.

Microcapsules are generally formed in a sequence of steps wherein a first component is combined with a second component, e.g., wherein an internal component is formed and a more exterior, surrounding component, is subsequently formed around the internal component. For example, a simple microcapsule (i.e., a non-composite microcapsule) can be formed as follows: a core containing living cells, e.g., a gel core, is formed, and a semipermeable coating is subsequently applied to the core. A simple or single composite microreactor can be formed as follows: internal particles containing living cells are formed, the internal particles are embedded in a surrounding super matrix, and (optionally) a semipermeable coating is subsequently applied to the internal particle-containing super matrix.

The inventors have discovered that the performance of a microcapsule can be improved if one or more of the components is geometrically stabilized, e.g., if an internal component is geometrically stabilized prior to the application of a more exterior, surrounding component. For example, the performance of a simple or single microcapsule can be improved by, prior to the application of a semipermeable membrane, allowing the gel core to become geometrically stabilized. The performance of a composite microcapsule can be improved, e.g., by, prior to embedding the internal particles in the super matrix, allowing the internal particles to become geometrically stabilized.

A geometrically stabilized component, as used herein, refers to a component that is treated such that it undergoes no substantial change in shape or volume when incorporated into a larger structure. In typical embodiments of the invention, a component, e.g., an interior or internal component, is geometrically stabilized prior to its incorporation into a larger structure. Generally, a component can be geometrically stabilized by allowing it to age for a period of time. For example, in embodiments of the invention a component is allowed to age prior to incorporating it into a larger structure or prior to depositing or otherwise forming a structure on its exterior surface. For example, a gel core can be geometrically stabilized, e.g., by aging, prior to depositing or forming a selectively permeable membrane on its outer surface; an internal particle can be geometrically stabilized, e.g., by aging, prior to its incorporation into a composite microreactor; and the super matrix of a composite can be geometrically stabilized, e.g., by aging, prior to depositing or forming a selectively permeable membrane on its outer surface. When a component, e.g., a gel, e.g., an alginate particle, is geometrically stabilized by aging, the aging period can be equal to or longer than 2 hours, equal to or longer than 12 hours, equal to or longer than 24 hours, equal to or longer than 36 hours, equal to or longer than 48 hours, equal to or longer than 3 days, or equal to or longer than 5 days. The geometric stabilization treatment should be such that viability or activity of the encapsulated material is not unacceptably altered and that the desirable properties of the component itself are not unacceptably compromised.

Although aging is the preferred method of geometric stabilization other methods can be used. For example, an alginate gel which has been treated with $CaCl_2$ can be further treated with a metal ion, e.g., a Ba or Fe ion, to geometrically stabilize the gel. A gel core can also be stabilized by cross-linking its surface.

A component is geometrically stabilized when any of the following conditions is met:

(1) it will undergo no substantial change (a substantial change is one which compromises the performance, e.g., the ability to exclude host cells) in shape or volume when the component is subjected to the next stage of the manufacturing process;

(2) when it is incorporated into a larger structure it induces fewer structural faults, or reduces the performance (e.g., the ability to immunoisolate) of the structure to a lesser degree, than would be the case if a non-geometrically stabilized, but otherwise similar, component were used (the presence of structural faults can be determined by microscopic examination or by the ability to inhibit passage of a test component, e.g., a molecule or cell; the ability to immunoisolate can be determined, in vivo, by implanting the structure in question in an animal and determining if the structure is capable of immunoisolation and resisting fibrotic inactivation, or in vitro, by incubating the structure with molecules of the immune system of a test animal);

(3) the component appears stable, in terms of shape and size, for at least 12 hours.

The method described above can be used to determine if a treatment is suitable for geometrically stabilizing a component.

Accordingly, in another aspect, the invention features a method of improving the performance of a microcapsule. The method includes:

(a) forming a first component of a microcapsule, (e.g., a core, e.g., a gel core);

(b) treating the first component so as to geometrically stabilize the first component (e.g., by allowing the first component to age for at least 12 hours); and (c) combining the geometrically stabilized first component with a second component of a microcapsule, (e.g., forming an exterior component, e.g., a semipermeable coating, around a geometrically stabilized gel core). In preferred embodiments step c is performed after step b.

In preferred embodiments the first component is: a core, e.g., a gel core, e.g., an alginate core; an internal particle matrix; an internal particle; a super matrix; a particle; a particle matrix.

In preferred embodiments the second component is: a coating; a matrix, e.g., a particle matrix or a super matrix; a component of a higher order composite.

In preferred embodiments: the first component is a gel core or matrix and the second component is a coating; the first component is a particle or an internal particle and the second component is a coating; the first component is a particle or internal particle and the second component is a matrix, particle matrix, or super matrix.

In preferred embodiments one of the components, e.g., the first component, contains a source of a therapeutic substance.

In preferred embodiments the first component is a gel matrix, e.g.,: a gel, e.g., a hydrogel, e.g., an alginate or agarose gel. In preferred embodiments the gel matrix is other than a liquid. The gel matrix can include substances which impede the passage of recipient-derived molecules or cells, e.g., it can include polyethylene oxide (PEO), polystyrene sulfonic acid (PSA), or polyornithine (PLO).

In preferred embodiments the gel matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the first component is a gel matrix having a coating. In more preferred the coating is or includes: a polyaminoacid, e.g., polylysine (PLL) or PLO; a naturally occurring substance, e.g., chitosan; a synthetic polymer e.g., PAN-PVC. A particularly preferred coating is polyamino acid, e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the second component is a matrix. In more preferred embodiments the matrix is or includes: a gel, e.g., a hydrogel, e.g., an alginate or agarose gel. In preferred embodiments the super matrix is other than a liquid. The matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the second component is a coating. In more preferred embodiments the coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiment the first component is geometrically stabilized by aging. In preferred embodiments the aging period is: equal to or greater than 2 hours, 6 hours, 12 hours, 24 hours, 48 hours, 4 days, 5 days, 7 days, 10 days, and 14 days. In more preferred embodiments the first component is allowed to age for between 2 hours and 14 days, e.g., for between 12 hours and 4 or 5 days.

In preferred embodiments the first component has a lower molecular weight exclusion number than does the second component, e.g., the first component excludes recipient immune molecules, e.g., IgG or complement, and the second component, allows immune molecules, e.g., IgG, or complement, to pass but excludes the passage of recipient cells.

In preferred embodiments: the outer surface of the composite is biologically compatible, e.g., it is sufficiently smooth that it inhibits fibrotic encapsulation of the composite, but the surface of the internal particle is not biologically compatible, e.g., it is not sufficiently smooth to inhibit fibrotic encapsulation.

In preferred embodiments the method includes
(a) forming a gel core containing a living cell, e.g., an islet cell;
(b) aging the gel core for between 2 hours and 5 days; and
(c) forming a semipermeable coating around the geometrically stabilized gel core), wherein step c is performed after step b.

In preferred embodiments the microcapsule is a double composite microreactor and: the first component is an internal particle and the second component is an internal particle coating; the first component is an internal particle and the second component is a particle matrix; first component is an internal particle coating and the second component is a particle matrix; first component is a particle and the second component is a particle coating; first component is a particle and the second component is a super matrix; first component is a particle coating and the second component is a super matrix; first component is a super matrix and the second component is an outer coating.

In preferred embodiments the outer component of the microcapsule, i.e., the component in contact with the recipient, is at least 50, 75, 90, 95, 97, or 98%, water.

In another aspect, the invention features, a method of improving the performance of a composite microreactor. The method includes:
(a) forming a first component of a composite microreactor, (e.g., a coated or uncoated internal core, e.g., an internal gel core);
(b) combining the first component with a second component of a composite microcapsule, (e.g., embedding the internal core in a super matrix, e.g., a gel super matrix); and performing one or both of the following steps (c) and (d):
(c) prior to combining the first and the second component, geometrically stabilizing the first component, (e.g., prior to embedding an internal core in a super matrix, treating the internal core so as to geometrically stabilize the internal core); and/or
(d) prior to combining the first and the second component with a third component, geometrically stabilizing the second component, (e.g., geometrically stabilizing a super matrix prior to forming an exterior component around the stabilized super matrix).

In preferred embodiments the first component is: a core, e.g., a gel core, e.g., an alginate core; an internal particle matrix; an internal particle; a super matrix; a particle; a particle matrix.

In preferred embodiments the second component is: a coating; a matrix, e.g., a particle matrix or a super matrix; a component of a higher order composite.

In preferred embodiments: the first component is a gel core or matrix and the second component is a coating; the first component is a particle or an internal particle and the second component is a coating; the first component is a particle or internal particle and the second component is a matrix, particle matrix, or super matrix.

In preferred embodiments one of the components, e.g., the first component, contains a source of a therapeutic substance.

In preferred embodiments the first component is a gel matrix, e.g., a gel, e.g., a hydrogel, e.g., an alginate or agarose gel. In preferred embodiments the gel matrix is other than a liquid. The gel matrix can include substances which impede the passage of recipient-derived molecules or cells, e.g., it can include polyethylene oxide (PEO), polystyrene sulfonic acid (PSA), or polyornithine (PLO).

In preferred embodiments the gel matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the first component is a gel matrix having a coating. In more preferred the coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the coating hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the second component is a matrix. In more preferred embodiments the matrix is or includes: a gel, e.g., a hydrogel, e.g., an alginate or agarose gel. In preferred embodiments the matrix is other than a liquid. The matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the matrix hinders the passage, and preferably essentially completely prevents the passage of molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the second component is a coating. In more preferred embodiments the coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiment the first component is geometrically stabilized by aging. In preferred embodiments the aging period is: equal to or greater than 2 hours, 6 hours, 12 hours, 24 hours, 48 hours, 4 days, 7 days, 10 days, and 14 days. In more preferred embodiments the first component is allowed to age for between 2 hours and 14 days, e.g., for between 12 hours and 4 or 5 days.

In preferred embodiments the first component has a lower molecular weight exclusion number than does the second component, e.g., the first component excludes recipient immune molecules, e.g., IgG or complement, and the second component, allows immune molecules, e.g., IgG, or complement, to pass but excludes the passage of recipient cells.

In preferred embodiments: the outer surface of the composite is biologically compatible, e.g., it is sufficiently smooth that it inhibits fibrotic encapsulation of the composite, but the surface of the internal particle is not biologically compatible, e.g., it is not sufficiently smooth to inhibit fibrotic encapsulation.

In preferred embodiments the second component is geometrically stabilized by aging. In preferred embodiments the aging period is: equal to or greater than 2 hours, 6 hours, 12 hours, 24 hours, 48 hours, 4 days, 7 days, 10 days, and 14 days; In more preferred embodiments the first component is allowed to age for between 2 hours and 14 days, e.g., for between 12 hours and 4 or 5 days.

In preferred embodiments the third component is a matrix. In more preferred embodiments the matrix is or includes: a gel, e.g., a hydrogel, e.g., an alginate or agarose gel. In preferred embodiments the matrix is other than a liquid. The matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the third component is a coating. In more preferred embodiments the coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, or about 5 kDa to less than about 10 kDa, e.g., 9 kDa–10 kDa, e.g., 9.7 kDa. Preferred coatings are volume-reducing coatings.

In preferred embodiments the coating hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the second component has a lower molecular weight exclusion number than does the third component, e.g., the second component excludes recipient immune molecules, e.g., IgG or complement, and the third component, allows immune molecules, e.g., IgG, or complement, to pass but excludes the passage of recipient cells.

In preferred embodiments the composite microreactor is a component of a higher order composite, e.g., a double composite, or a third order composite.

In a preferred embodiment, the method further includes incorporating the composite into a higher order composite, e.g., a double composite. In more preferred embodiments, the composite is geometrically stabilized prior to incorporating it into a higher order composite, e.g., a double composite. For example, an internal alginate particle coated with polylysine of between about 1 kDa–4 kD and containing a living cell, e.g., an islet, is formed. The internal particle is aged for between about 3–5 days prior to incorporating it into an alginate particle matrix. The aged internal particle is then incorporated into a particle matrix. The particle matrix is then coated with polylysine of between about 5 kDa to less than about 15 kD, and is aged for between about 2–24 hours. Finally, the aged coated particle is embedded into an alginate matrix to form a double composite.

In preferred embodiments the composite microreactor is a double composite microreactor and: the first component is an internal particle and the second component is an internal particle coating; the first component is an internal particle and the second component is a particle matrix; first component is an internal particle coating and the second component is a particle matrix; first component is a particle and the second component is a particle coating; first component is a particle and the second component is a super matrix; first component is a particle coating and the second component is a super matrix; first component is a super matrix and the second component is an outer coating.

In preferred embodiments the outer component of the composite microreactor, i.e., the component in contact with the recipient, is at least 50, 75, 90, 95, 97, or 98%, water.

The inventors have also discovered that application of a coating of a relatively low molecular weight polymer, e.g., a relatively low molecular weight polyamino acid, to a microcapsule component, e.g., to a core, e.g., a gel core or a super matrix, can result in a decrease in the diameter and volume of the resulting coated component.

Accordingly, in another aspect, the invention features, a method of making a microcapsule having reduced volume. The method includes:

(a) forming a component of a microcapsule, (e.g., a core particle, e.g., a gel particle); and (b) applying a volume reducing coating to the component, thereby producing a microcapsule including a component and a coating and having a volume less than the volume of the uncoated component.

In preferred embodiments the volume reducing coating is or includes: a polyamino acid, e.g., polylysine, or polyornithine, having a molecular weight of less than 15 kDa, more preferably of less than 10 kDa, more preferably of less than 5 kDa. Particularly preferred are polyamino acids with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa.

In preferred embodiments the component is a gel matrix, e.g.,: a gel, e.g., a hydrogel, e.g., an alginate or agarose gel. In preferred embodiments the gel matrix is other than a liquid. The gel matrix can include substances which impede the passage of recipientderived molecules or cells, e.g., it can include polyethylene oxide (PEO), polystyrene sulfonic acid (PSA), or polyornithine (PLO).

In preferred embodiments the gel matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the component is a gel matrix having a coating. In more preferred the coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings. In preferred embodiments the coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the component contains a source of a therapeutic substance.

In preferred embodiments the microcapsule is incorporated into a composite, e.g. a double, or higher order composite.

In preferred embodiments the coating is geometrically stabilized prior to being implanted in a recipient.

In preferred embodiments the method includes HTP-00 1

(a) forming a gel core containing a living cell, e.g., an islet cell;

(b) forming a relatively low molecular weight polyamino acid coating on the core.

In preferred embodiments the outer component of the microcapsule, i.e., the component in contact with the recipient, is at least 50, 75, 90, 95, 97, or 98%, water.

In another aspect, the invention features, a method of making a composite microreactor having reduced volume. The method includes:

(a) forming a first component of a composite microreactor, (e.g., forming an internal core particle, e.g., an internal gel particle);

(b) combining the first component with a second component of a composite microreactor, (e.g., embedding an internal core particle in a super matrix, e.g., a gel super matrix); and performing one or both of the following steps (c) and (d):

(c) prior to combining the first component with the second component, applying a volume reducing coating to the first component, (e.g., prior to embedding an internal core particle in a super matrix, applying a volume reducing coating of low molecular weight polylysine to the core particle); and/or (d) applying a volume reducing coating to the second component, (e.g., applying a volume reducing coating to the super matrix), thereby producing a composite microreactor having a reduced volume.

In preferred embodiments the volume reducing coating is or includes: a polyamino acid, e.g., polylysine, or polyornithine, having a molecular weight of less than 15 kDa, more preferably of less than 10 kDa, more preferably of less than 5 kDa. Particularly preferred are poly amino acids with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa.

In preferred embodiments the first component is: a core, e.g., a gel core, e.g., an alginate core; an internal particle matrix; an internal particle; a super matrix; a particle; a particle matrix.

In preferred embodiments the second component is: a coating; a matrix, e.g., a particle matrix or a super matrix; a component of a higher order composite.

In preferred embodiments: the first component is a gel core or matrix and the second component is a coating; the first component is a particle or an internal particle and the second component is a coating; the first component is a particle or internal particle and the second component is a matrix, particle matrix, or super matrix.

In preferred embodiments one of the components contains a source of a therapeutic substance.

In preferred embodiments the first component is a gel matrix, e.g.: a gel, e.g., a hydrogel, e.g., an alginate or agarose gel. In preferred embodiments the gel matrix is other than a liquid. The gel matrix can include substances which impede the passage of recipientderived molecules or cells, e.g., it can include polyethylene oxide (PEO), polystyrene sulfonic acid (PSA), or polyornithine (PLO).

In preferred embodiments the gel matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the first component is a gel matrix having a coating. In more preferred the coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the coating hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the second component is a matrix. In more preferred embodiments the matrix is or includes: a gel, e.g., a hydrogel, e.g., an alginate or agarose gel. In preferred embodiments the matrix is other than a liquid. The matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the second component is a coating. In more preferred embodiments the coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Preferred coatings are volume-reducing coatings.

In preferred embodiments the coating hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiment the first component is geometrically stabilized by aging. In preferred embodiments the aging period is: equal to or greater than 2 hours, 6 hours, 12 hours, 24 hours, 48 hours, 4 days, 7 days, 10 days, and 14 days; In more preferred embodiments the first component is allowed to age for between 2 hours and 14 days, e.g., for between 12 hours and 4 or 5 days.

In preferred embodiments the first component has a lower molecular weight exclusion number than does the second component, e.g., the first component excludes recipient immune molecules, e.g., IgG or complement, and the second component, allows immune molecules, e.g., IgG, or complement, to pass but excludes the passage of recipient cells.

In preferred embodiments: the outer surface of the composite is biologically compatible, e.g., it is sufficiently smooth that it inhibits fibrotic encapsulation of the composite; the outer surface of the composite is biologically compatible, e.g., it is sufficiently smooth that it inhibit fibrotic encapsulation of the composite but the surface of the internal particle is not biologically compatible, e.g., it is not sufficiently smooth to inhibit fibrotic encapsulation.

In preferred embodiment the second component is geometrically stabilized by aging. In preferred embodiments the aging period is: equal to or greater than 2 hours, 6 hours, 12 hours, 24 hours, 48 hours, 4 days, 7 days, 10 days, and 14 days; In more preferred embodiments the first component is allowed to age for between 2 hours and 14 days, e.g., for between 12 hours and 4 or 5 days.

In preferred embodiments the composite microreactor is a component of a higher order composite, e.g., a double composite, or a third order composite.

In a preferred embodiment, the method further includes incorporating the composite into a higher order composite, e.g., a double composite. In more preferred embodiments, a volume-reducing coating is applied to the composite (or one of its components) prior to incorporating it into a higher order composite, e.g., a double composite. For example, an internal agarose particle coated with polylysine of between about 1 kDa–4 kD and containing a living cell, e.g., an islet, is formed. The internal particle is then incorporated into the particle matrix. The particle matrix is then coated with polylysine of between about 5 kDa to less than about 15 kD. Finally, the coated composite is embedded into an agarose matrix to form a double composite.

In preferred embodiments the composite microreactor is a double composite microreactor and: the first component is an internal particle and the second component is an internal particle coating; the first component is an internal particle and the second component is a particle matrix; first component is an internal particle coating and the second component is a particle matrix; first component is a particle and the second component is a particle coating; first component is a particle and the second component is a super matrix; first component is a particle coating and the second component is a super matrix; first component is a super matrix and the second component is an outer coating.

In preferred embodiments the outer component of the composite microreactor, i.e., the component in contact with the recipient, is at least 50, 75, 90, 95, 97, or 98%, water.

The inventors have also discovered that a high molecular weight molecule, e.g., a polymer, e.g., PEO, can be added to a microcapsule to improve its immunoisolating properties. Because of its high molecular weight, the molecule does not need an outer coating to prevent it from leaking out of the matrix, yet the molecule does not result in unacceptable viscosity.

Accordingly, in another aspect, the invention features, a microcapsule, e.g., a composite microreactor as described herein, which includes:

a source of a therapeutic substance, a molecule, e.g., a polymer, e.g., PEO, of at least 1–8 million Da in molecular weight, and a matrix, the source and the molecule of at least 1–8 million Da embedded in the matrix.

In preferred embodiments the matrix does not have an outer coating.

In preferred embodiments the matrix is or includes: a gel, e.g., a hydrogel, e.g., an alginate or agarose gel. In preferred embodiments the matrix is other than a liquid. The matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the matrix hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the outer component of the microcapsule, i.e., the component in contact with the recipient, is at least 50, 75, 90, 95, 97, or 98%, water.

The inventors have also discovered that it is not necessary to reliquify the gel matrix of a microcapsule, e.g., the internal matrix, particle matrix, or super matrix of a composite microreactor as described herein. Allowing the matrix to remain a gel eliminates the liquefaction step, preserves the immunoisolating properties of the matrix, and does not unacceptably hinder diffusion or cell viability.

Accordingly, in another aspect, the invention features, a microcapsule, e.g., a composite microreactor as described herein, which includes:

a source of a therapeutic substance, and a matrix which is not a liquid.

In preferred embodiments the matrix is or includes: a gel, e.g., a hydrogel, e.g., an alginate or agarose gel. The matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the matrix hinders the passage, and preferably essentially completely prevents the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the outer component of the microcapsule, i.e., the component in contact with the recipient, is at least 50, 75, 90, 95, 97, or 98%, water.

In yet another aspect, the invention features, a single composite microreactor which includes:

(a) one, or a plurality, of an internal particle (preferably containing a living cell);

(b) optionally, an internal particle coating covering the internal particle;

(c) a matrix component in which the internal particle is embedded;

(d) optionally, an outer coating covering the matrix component, wherein, at least one component of the single composite microreactor is free of defects which arise from the inclusion of non-geometrically stabilized components.

In yet another aspect, the invention features, a double composite microreactor which includes:

(a) one, or a plurality, of an internal particle (preferably containing a living cell);

(b) optionally, an internal particle coating covering the internal particle;

(c) one, or a plurality, of a matrix component in which the internal particle is embedded;

(d) optionally, a particle or matrix coating covering the matrix component;

(e) a super matrix in which the matrix component is embedded;

(f) optionally, an outer coating covering the double composite, wherein at least one component of the double composite microreactor is free of defects which arise from the inclusion of non-geometrically stabilized components. In preferred embodiments one component of the double composite microreactor, e.g., the matrix component or its coating, is not free of defects which arise from the inclusion of non-geometrically stabilized components, but the super matrix is free of such defects.

In yet another aspect, the invention features, a method of implanting a living donor cell into a recipient. The method includes the steps of:

providing a microcapsule, e.g., a composite microreactor, of the invention which contains the living donor cell; and implanting the microcapsule into the recipient animal.

In preferred embodiments the method further includes testing the recipient for antibodies to the living cell. The test can be performed before or after the microcapsule is implanted.

In preferred embodiments no adjunctive immunosuppression is administered to the recipient.

In preferred embodiments the method further includes: administering to the recipient adjunctive immunosuppression for less than 30 days; the step of administering a drug to the host animal at a dosage effective to inhibit fibrosis and inflammation around the uncoated particle, but at a dosage lower than that required to achieve immunosuppression when the donor cell is implanted into the host animal without encapsulation, e.g., wherein the drug is cyclosporin A and is administered at a dosage that achieves a whole blood trough level of less than about 100 ng/ml in the host animal.

In preferred embodiments the cell is: a living cell; a eukaryotic cell, e.g., a rodent, canine, porcine, or human cell; a prokaryotic cell, e.g., a bacterial cell; a fungal or a plant cell; a cell which is genetically engineered, e.g., a cell which is genetically engineered to produce a protein, e.g., a human protein.

In preferred embodiments the cell is an autologous, an allogeneic, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci.

In preferred embodiments the recipient animal is a dog, a pig, or a human.

In preferred embodiments the donor cell is a pancreatic islet cell.

In preferred embodiments: the composite microreactor contains pancreatic islets, e.g., at e.g., a density of 5,000 to 100,000 islets per milliliter of medium; the composite microreactor contains living cells at a density of about $10^5$ to $10^8$ cells per milliliter of medium.

In preferred embodiments the recipient is suffering from a disorder, e.g., diabetes, caused by a deficient production of a substance, e.g., insulin, in the recipient and the donor cell provides a substance which treats the disorder.

In preferred embodiments the donor cell secretes Factor IX, Factor VIII, an interleukin, e.g., interleukin 2, an interferon, an endocrine hormone, a nerve growth factor, tumor necrosis factor alpha, a neurotropic factor, or a neurotransmitter.

In preferred embodiments the disorder is diabetes mellitus, hepatic disease, amyotrophic lateral sclerosis, hemophilia, hypothyroidism, Parkinson's disease, acquired immune deficiency syndrome, Duchenne's muscular dystrophy, infertility, epilepsy, Huntington's disease, hypoparathyroidism, a mood disorder, a motor neuron disease, osteoporosis, or Alzheimer's disease.

In preferred embodiments: the composite microreactors are implanted into an immunoprivileged site in the patient; the composite microreactors are implanted by injection.

In yet another aspect, the invention features, an artificial organ suitable for implantation into a mammal, which includes one or a plurality of an effective number of the composite microreactors of the invention.

In yet another aspect, the invention features, an insulin producing system, including a composite microreactor (including a living cell) in a culture medium, wherein the living cell is a mammalian islet of Langerhans cell, and wherein the culture medium comprises nutrients and amino acids sufficient to maintain the cell and allow the cell to synthesize insulin.

In yet another aspect, the invention features, an in vivo method of culturing a living cell, the method including the steps of: encapsulating the living cell in a microreactor of the invention, inserting the microreactor into an animal, e.g., a non human animal, and culturing the cell in the animal.

In yet another aspect, the invention features, a preparation of: a microcapsule which includes a living cell, e.g., a composite microreactor, of the invention, and a carrier suitable for implantation into a human. In preferred embodiments the preparation is contained in a device suitable to deliver the microcapsules to a recipient, e.g., a device for injection the preparation into a recipient.

In yet another aspect, the invention features, a microcapsule which includes a living cell, e.g., a composite microreactor, of the invention, in a culture medium which will support the living cell.

In yet another aspect, the invention features, a microcapsule which includes a living cell, e.g., a composite microreactor, made by a method described herein.

Microcapsules of the invention, e.g, single or double composites, are preferably less than 4,000, more preferably less than 3,500, 3,000, 2,500, 2,000, 1,500, or 1,000 microns in diameter.

In single composite microreactors of the invention, the thickness of the super matrix (i.e., the distance between the inner and outer surfaces of the super matrix) is preferably at least 10, 25, 50, 100, 150, 200, or 250 microns.

In double composite microreactors of the invention, the thickness of the particle matrix (i.e., the distance between the inner and outer surfaces of the particle matrix) is preferably at least 10, 25, 50, 100, 150, 200, or 250 microns; the thickness of the super matrix (i.e., the distance between the inner and outer surfaces of the super matrix) is preferably at least 10, 25, 50, 100, 150, 200, or 250 microns.

Microcapsules of the invention, e.g, single or double composites, are preferably more than 80, more preferably more than 100, 200, 400, 600, 800, 1,000, 1,200, 1,400, 2,000, 2,500, 3,000, 3,500, 4,000, 4,500, or 5,000 microns in diameter.

In single composite microreactors of the invention, the diameter of the internal particle is preferably more than 80, more preferably more than 100, 200, 400, 600, 800, 1,000, 1,500, or 2,000 microns. The diameter of the single composite microreactor is preferably more than 200, more preferably more than 400, 600, 800, 1,000, 1,200, 1,400, 2,000, 2,500, 3,000, 3,500, 4,000, 4,500, or 5,000 microns.

In double composite microreactors of the invention, the diameter of the internal particle is preferably more than 80, more preferably more than 100, 200, 400, 600, 800, 1,000, 1,500, or 2,000 microns. The diameter of the particle is preferably more than 100, more preferably more than 200, 400, 600, 800, 1,000, 1,500, 2,000, or 2,500 microns. The diameter of the double composite microreactor is preferably more than 200, more preferably more than 400, 600, 800, 900, 1,000, 1,200 1,400, 2,000, 2,500, 3,000, 3,500, 4,000, 4,500, or 5,000 microns.

As used herein, microcapsule refers to a source of a therapeutic substance enclosed in an applied semipermeable component, e.g., a matrix and/or a coating. The component is one which excludes one or more of IgG, complement, or cells.

As used herein, a source of a therapeutic substance can include a composition of matter which produces or releases a therapeutic substance, e.g., a protein, e.g., an enzyme, hormone, antibody, or cytokine, a sense or anti-sense nucleic acid, e.g, DNA or RNA, or other substance which can exert a desired effect on a recipient. The therapeutic substance can also be a composition of matter which absorbs or modifies or detoxifies a substance produced by the recipient. The source of a therapeutic substance can be a tissue or a living cell; a eukaryotic cell, e.g., a rodent, canine, porcine, or human cell; a prokaryotic cell, e.g., a bacterial cell; a fungal or plant cell; a cell which is genetically engineered, e.g., a cell which is genetically engineered to produce a protein, e.g., a human protein. The source of a therapeutic substance can be or include an autologous, an allogeneic, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci.

Many clinically useful cells, e.g., normal pancreatic islets, cannot presently be efficiently propagated in culture. This, together with a relative shortage of human donor tissue, means that widespread clinical transplantation of such cells, e.g., to treat diabetes, will likely require the use of discordant xenografts. The invention allows transplantation of microencapsulated allogeneic or xenogeneic donor tissue, even discordant xenogeneic tissue, with little or no adjunctive immunosuppressive therapy.

Composite microreactors of the invention allow the use of internal particle coatings which are not biocompatible, e.g., polyacrylate or plastics. Methods of the invention allow the use of virtually any material which can be used to form permselective barriers, e.g., materials such as, chitosan, polyacrylate, or synthetic polymers, which alone might be digested by enzymes, or which might trigger a fibrotic response when they come into direct contact with host tissues. Furthermore, microcapsules of the invention having an outer hydrogel coating inhibit the scarring of organs which often accompanies the long-term use of hard plastic shells.

The geometrically stabilized microcapsules of the invention have improved performance characteristics. For example, they are more resistant to invasion by components of the host immune system. Geometrically stabilized microcapsules are also more effective in preventing release of implant antigens, and thereby help to minimize the host's anti-implant response.

Embodiments of the invention feature the use of coatings, which result in a decrease in the volume of the coated particle. These coatings are referred to herein as volume-reducing coatings. The use of volume-reducing coating confers a number of advantages on a microcapsule, e.g., a composite microreactor. With many prior art encapsulation methods, the encapsulation of a number of cells which is sufficient to provide a sustainable biological effect in the host results in an undesirably large volume. Use of the volume-reducing methods and materials of the invention allows a useful number of cells to be delivered in a smaller volume. The use of volume-reducing coatings, e.g., low molecular weight polylysine, can result in a 30% decrease in diameter of the internal particle (with an even greater percent reduction in volume of the particle). Without the use of volume-reducing methods, the volume of the encapsulated beads can give a greater than 300% increase in the volume of the particles. For example, a 30% increase in diameter gives a 3-fold increase in volume.

The use of smaller microcapsules can also reduce the risk of producing a fibrotic response. There are two types of fibrotic responses, an acute response and a chronic response. The acute response is generated in large part by the degree of smoothness of the exterior surface of the microcapsule. The introduction of a microcapsule having a rough surface will trigger a relatively rapid fibrotic response. An acute response can usually be avoided by the use of a microcapsule having a smooth exterior surface. The size of a microcapsule plays a large part in the generation of a chronic fibrotic response. A smooth surface microcapsule, if it has a diameter of about 2 mm or more, will, after a few weeks or months, often elicit a chronic response. By using a volume-reducing coating, relatively small, preferably smaller than or about equal to 1 mm in diameter, single or even double composite microreactors can be produced. Furthermore, the volume reducing coating will allow for easier preparation of microcapsules, e.g., composite microreactors, as smaller microcapsules are generally easier to produce.

The reduced size microcapsules of the invention can contribute to sustaining the viability of encapsulated cell. Microcapsules having a relatively large diameter, e.g., a radius of greater than 0.5 mm generally make it more difficult for the encapsulated cells to exchange necessary nutrients and oxygen with the outside environment. This can result in premature cell death. Again, by use of a volume reducing coating, the diameter of single, or double composite microreactors can be minimized and thereby prolong the period for which an encapsulated cells is viable.

The composite microreactors of the invention allow important properties of the composite microreactors to be allocated or partitioned to different components of the composite microreactor, thereby allowing the properties to be optimized. For example, it has been found that although the use of lower weight polyamino acids as coatings results in a more effective barrier to molecules of the host's immune system, e.g., IgG, these coating are sometimes associated with undesirable properties. For example, they can have surfaces which do not effectively inhibit fibrosis and they are often not geometrically stable just after manufacture and can thus introduce faults in other components of the composite microreactor. As is discussed herein, the inventors have found that geometrically stabilizing the internal particles can minimize the induction of faults and that the inability to inhibit fibrosis can be overcome by using such surfaces as an internal component of a composite microreactor, but not on the surface which faces the body of the recipient.

The inventors have also discovered that the tendency of certain components, e.g., low molecular weight polyamino acids to induce faults, or to otherwise compromise performance, can be countered not only by geometric stabilization, but by using such coatings on the most internal components of a microcapsule. For example, in the case of a double composite, these materials can be used as coatings on the internal particles. The internal particle coating is separated from the host by the particle matrix, the particle coating (if present), the super matrix, and, the outer coating (if present). Even if the internal particle coating induces a fault in the particle matrix, the particle coating (if present), the super matrix, and the outer coating (if present) still hinder the passage of host components, e.g., host cells.

This approach is particularly advantageous when it is desirable to minimize the amount of time taken by geometric stabilization. Prolonged cell culture is not compatible with viability in all cell types. Some cells, e.g., some primary cells, can survive in the host but cannot survive for extended periods in culture. Stabilization generally takes longer the lower the molecular weight of the coating. For example, in the conditions described herein, substantial stabilization of 5 kDa to less that 15 kDa polylysine coatings takes about a day, while substantial stabilization of 1 kDa–4 kDa, about 1 kDa-less than 4 kDa coatings takes 3–5 days). Thus, in some applications it is desirable both to use a geometrically "unstable" component (or at least to minimize the amount of stabilization time) and to minimize the "culture" time of the source, e.g., a cell, to be delivered. In embodiments of the invention, performance is improved by using a double composite in which the internal particle coating provides protection from smaller species, e.g., molecules as opposed to cells, e.g., IgG molecules, while other components e.g., the particle coating and/or super matrix, while not providing a barrier to smaller species, provide a barrier to large species, e.g., cells. Thus, in embodiments of the invention, the component which provides protection from the smaller species, and which may induce faults in an adjacent component, is separated from the component(s) (e.g., the particle coating and super matrix) which provide protection from invading cells, by an intervening, or "buffer" component, e.g., the particle matrix. Thus even if the internal particle coating induces faults in the particle matrix, the particle coating and/or super matrix prevent contact of cells with the internal particle coating (which is often not anti-fibrotic).

If polylysine of about 1 kDa–4 kDa is used on the internal particles, and a less unstable coating, e.g., a coating of about 5 kDa to less than 15 kDa, or of about 5 kDa to less than about 10 kDa, is used on the particle, a geometric stabilization of as little as about 24 hours can be used with the internal particle. A particularly effective composite uses a polyamino acid, e.g., polylysine, of less than 5 kDa as the internal particle coating and a polylysine of about 9 kDa–10 kDa as the particle coating. The diameter of the internal particle is about 300 microns, the particle about 600 microns, and the entire composite about 900 microns.

Composite microreactors of the invention have reduced size, and can therefore have reduced size and allow delivery by injection. For example, composite microreactors of about 1,000 microns or less in diameter can be delivered with a 16 gauge needle. Larger microreactors, e.g., those of 1,500 microns in diameter, generally require larger needles.

The release of small components, e.g., cytokines, NO, and other toxic moieties by recipient immune cells plays an important role in the inactivation of implanted donor tissue. Microcapsules of the art often possess only a thin barrier, e.g., a polylysine coating and/or a thin electrostatic exterior coating of agarose, between the encapsulated cells and recipient cells. Even though recipient cells may be denied direct contact with the encapsulated cells, the recipient cells can come into close enough proximity such that small molecules (which pass through any semipermeable membrane present on the microcapsule) they release are present in sufficient concentration inside the microcapsule to damage the encapsulated cells. Composite microreactors of the invention can include one or more components which, separately or together, are of sufficient diameter, or of sufficient thickness, such that they provide a substantial distance between recipient cells, e.g., lymphocytes, macrophages, or NK cells, and the source of a therapeutic substance The distance is sufficient such that exposure of the source to small molecules e.g., cytokines, NO, and other toxic moieties, released by recipient cells, is substantially reduced by diffusion. Composite microreactors of the invention can thus minimize the concentration of recipient cell-released small molecules and thereby promote the viability or function of the encapsulated cells.

The release of donor antigens, e.g, proteins, into the recipient, or into outer components of the composite which might contain recipient cells, can stimulate a recipient immune response to donor antigens. Composite microreactors of the invention can include one or more components which, separately or together, are of sufficient diameter, or of sufficient thickness, such that they provide a substantial distance or separation between antigens released by the source and recipient cells, e.g., lymphocytes, macrophages, or NK cells. The distance is sufficient such that diffusion, or trapping in the matrix of the component or components which provide the separation, substantially reduces exposure of recipient cells to released antigens. This is particularly important in inhibiting recipient cell to donor antigen contact in the case of acute release of donor antigen, e.g., the release of comparatively large amounts of antigen over a short time as a result of cell death. The matrix of the component or components which supply the separation can also act to inhibit diffusion of larger protein antigens which are efficiently processed into antigenic species by the recipient. The distance also minimizes the contact of cells of the recipient with donor antigen, e.g., proteins, which protrude from or extend through one or both of the internal particle matrix or internal particle coating. Composite microreactors of the invention can thus minimize the recipient response to donor antigens. This is particularly important because once the recipient is sensitized to a particular donor species it is much more difficult to provide successful encapsulation in subsequent implantations.

Composite reactors of the invention, because they allow sources to be sequestered within internal particles, can prevent the protrusion of sources through the outer surface of the composite.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the following detailed description and from the claims.

BRIEF DESCRIPTION OF THE DRAWINGS

FIG. 1 is a schematic diagram of a composite microreactor.

FIG. 2 is a schematic diagram of a double composite microreactor.

DETAILED DESCRIPTION OF THE INVENTION

Composite Microreactors

A microcapsule should possess a variety of diverse properties if it is to preserve the viability of the encapsulated material, allow rapid, timely and adequate release of donor tissue produced substances, and satisfy other clinical requirements. The microcapsule should possess the following properties:

(1) it should allow relatively efficient diffusion of critical nutrients from the recipient environment into the microcapsule;

(2) it should allow relatively efficient diffusion of donor cell waste products out of the microcapsule;

(3) it should allow efficient diffusion of recipient signal molecules, e.g., in the case of the treatment of diabetes, glucose, into the microcapsule;

(4) it should allow diffusion of the critical substance supplied by the encapsulated cells, e.g., in the case of the treatment of diabetes, insulin, into the recipient milieu;

(5) it should minimize non-immune inactivation, e.g., by fibrotic encapsulation, of the microcapsule;

(6) it should minimize contact of the recipient's immune system with the encapsulated cells;

(7) it should have a life time of about the same length as the encapsulated cells;

(8) it should use, to the extent possible, biocompatible materials;

(9) it should be biocompatible with respect to the graft or islet tissue; and

(10) it should minimize release, particularly acute release, of antigens which might stimulate a recipient immune response.

Although some of these properties, e.g., 4, 5, and 6, must be possessed by a microcapsule, the properties need not be possessed by all components of the microcapsule. E.g., internal components need not be anti-fibrotic and not every element of the device needs to be effective in inhibiting the passage of recipient immune components, e.g., Ig molecules or complement; or recipient-derived cells. As described in more detail below, the multicomponent structure of the composite microreactors of the invention allow segregation of functions and properties and thus allow greater freedom in the choice of materials and greater efficacy of the microcapsule.

Structural Components

Figure 1:
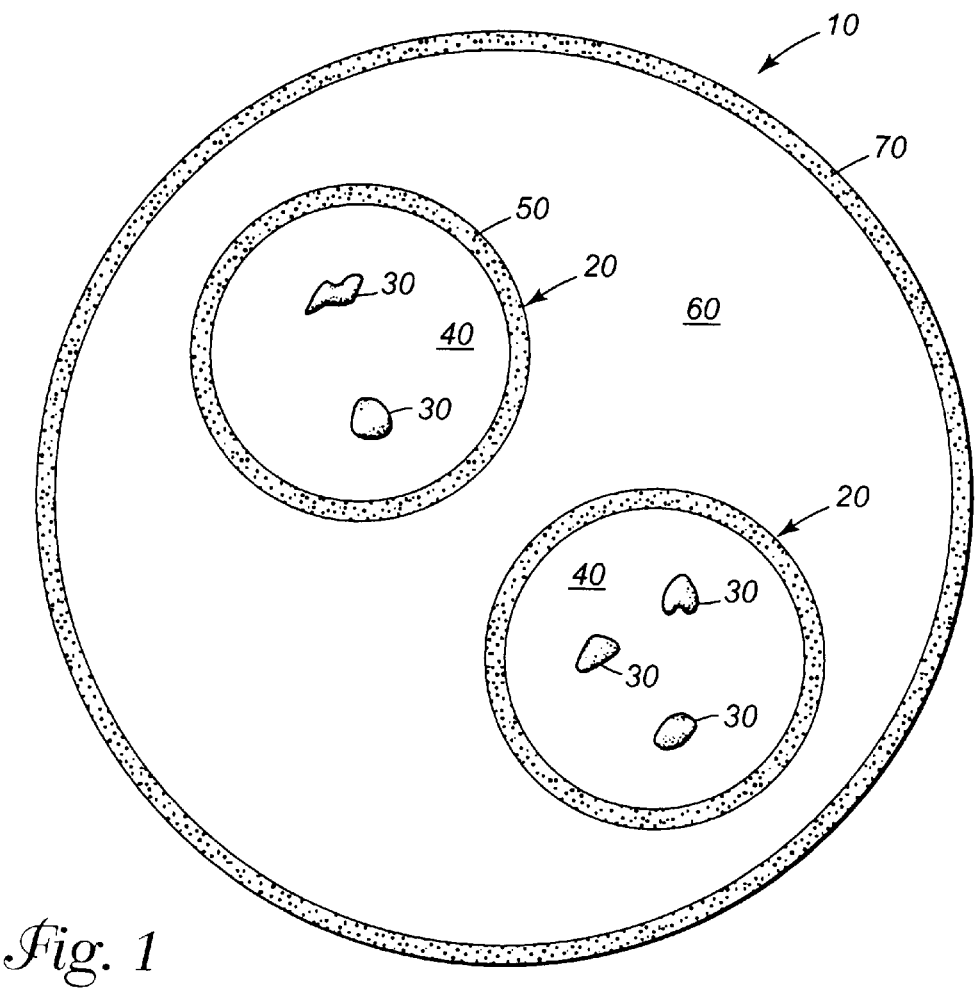

FIG. 1 is a schematic diagram of a simple or single composite microreactor (10). The composite microreactor (10) contains at least one, and preferably a plurality of internal particles (20). An internal particle (20) includes one or a plurality of sources (30) of a therapeutic or otherwise desirable substance. The sources (30) are embedded carried on, adhered to, or in an internal particle matrix (40). The internal particle (20) can optionally include an internal particle coating (50). The internal particles can be embedded in a super matrix 60. The composite microreactor 10 can (optionally) include an outer coating 70.

The diameter of the composite microreactor (10) is preferably between 100 microns and 4 millimeters, between 300 and 1200 microns, between 300 and 1500 microns, between 400 and 1000 microns, or between 400 and 800 microns. More preferably the diameter is about 600 microns.

The diameter of the internal particles (20) before application of a volume-reducing coating (described below) is preferably between 50 and 700 microns, more preferably between 100 and 500 microns, more preferably between 200 and 400 microns, and most preferably about 300 microns in diameter. The diameter of the internal particles (20) after application of a volume-reducing coating (described below) is preferably between 35 and 500 microns, more preferably between 75 and 400 microns, more preferably between 100 and 300 microns, and most preferably about 200 microns in diameter.

As is discussed in more detail elsewhere herein, the source 30 can be a cell, or a group of cells, e.g., an islet. The sources of an internal particle can all be of one type or more than one type of source can be included in an internal particle. Furthermore, the composite microreactor 10 can include more than one type of internal particle (20), e.g., the composite microreactor 10 can include a first type of internal particle (20) having within it a first source, e.g., a first type of cell, and a second type of internal particle (20) having within it a second source, e.g., a second type of cell.

The internal particle matrix (40) can be a gel, e.g., a hydrogel, e.g., alginate or agarose. The internal particle matrix can also be a solid particle, e.g., a glass bead, or a porous structure, on which anchorage dependent cells can be seeded. The internal matrix (40) can have immunoisolative properties. In some embodiments it has little or no ability to exclude low molecular weight species, e.g., IgG or complement, with this property being relegated to other components of the composite microreactor (10). The internal particle matrix (40) can be rendered immunoisolating by controlling its porosity, e.g., such that it hinders the passage of molecules of relatively large molecular weight, or by adding to it components, e.g., polyethylene oxide (PEO), polystyrene sulfonic acid (PSA), or polyornithine (PLO) which hinder the passage of molecules of relatively large molecular weight. Regardless of the method of controlling its permeability, the internal matrix (40) will, in preferred embodiments, hinder the passage, and preferably, essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells. The internal matrix (40) need not be anti-fibrotic and need not be biocompatible. The composite microreactor (10) can include more than one type of internal particle (20), e.g., the composite microreactor (10) can include a first type of internal particle (20) having within it a first type of internal matrix (40) and a second type of internal particle (20) having within it a second type of internal matrix (40).

The internal particle coating (50) is optional. It can be made of a polyaminoacid, e.g., polylysine (PLL), PLO, chitosan, or PAN-PVC, or any coating used to coat non-composite microreactors. In addition, the coating can be formed by modifying the structure of the matrix, e.g., the matrix can be cross-linked, e.g., with metal ions, e.g., Ba or Fe ions, or by photo-cross-linking, to form an coating. A preferred coating is polylysine having a molecular weight of less than 15 kDa, more preferably of less than 10 kDa, more preferably of less than 5 kDa. Particularly preferred are polylysines with a molecular weight of about 3–4 kDa, e.g., 3.7 kDa, or about 9 kDa–10 kDa, e.g., 9.7 kDa. Preferred coatings are volume-reducing coatings. Furthermore, the composite microreactor 10 can include more than one type of internal particle (20), e.g., the composite microreactor 10 can include a first type of internal particle (20) having a first type of internal particle coating and a second type of internal particle (20) having a second type of internal particle coating (50). Because, in some embodiments, the internal particles coating (50) need not be biocompatible and need not be anti-fibrotic, other properties of the internal coating (50), e.g., its ability to immunoisolate, can be optimized without the necessity of any compromise to confer biocompatibility or anti-fibrotic activity.

Super matrix (60) can be a gel, e.g., a hydrogel, e.g., alginate or agarose. The super matrix (60) can have immunoisolative properties. In some embodiments it can have little or no ability to exclude low molecular weight species, e.g., IgG or complement, with this property being relegated to other components of the composite microreactor (10). The super matrix (60) can be rendered immunoisolating by controlling its porosity, e.g., such that it hinders the passage of molecules of relatively large molecular weight or by adding to it components, e.g., PEO, PSA, or PLO which hinder the passage of relatively large molecules. Regardless of the method of controlling its permeability, the super matrix (60) will in preferred embodiments, hinder the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells. The super matrix (60) need not be anti-fibrotic and need not be biocompatible if a more proximal or more exterior component supplies these functions.

Outer coating (70) is optional. It can be made of a polyaminoacid, e.g., PLL or PLO, chitosan, or PAN-PVC, or any coating used to coat non-composite microreactors. Alternatively, the coating can be formed by modifying the structure of the matrix, e.g., the matrix can be cross-linked, e.g., with metal ions, e.g., Ba or Fe ions, or by photo-cross-linking, to form an coating. A preferred coating is polylysine having a molecular weight of less than 15 kDa, more preferably of less than 10 kDa, more preferably of less than 5 kDa. Particularly preferred are polylysines with a molecular weight of about 3–4 kDa, e.g., 3.7 kDa, or about 9 kDa–10 kDa, e.g., 9.7 kDa. Preferred coatings are volume-reducing coatings. The outer coating (70) need not be immunoisolating if other components supply this function.

The multi-component structure of the composite microreactor allows selection of materials which can optimize performance. Coating materials which are highly immunoisolating, but less desirable in terms of their biocompatibility or anti-fibrotic activities, can be used in the internal particle coating. The multi-component structure also allows for multiple lines of defense against invasion by recipient immune system components. E.g., the use of an outer coating which passes 1 in $10^2$ recipient IgG molecules, a super matrix which passes 1 in $10^2$ recipient IgG molecules, and an internal particle coating which passes 1 in $10^2$ recipient IgG molecules, results in a composite pass rate of only about 1 in $10^6$.

The ability to segregate functions also allows construction of composite microreactors the life of which are roughly commensurate with the useful life of the enclosed sources. For example, gelatin, which weakens the matrix, could be added. If it is necessary to strengthen the matrix, fibers can be added.

A preferred composite microreactor is one in which: the composite microreactor contains at least two internal particles; the source of a therapeutic or otherwise desirable substance is a cell, e.g., an islet cell; the internal particle matrix is alginate; the internal particle includes an internal particle coating of polylysine; the internal particles are embedded in a super matrix of alginate; and the composite microreactor includes an outer coating of polylysine; the polylysine of the internal particle coating is of a molecular weight of between 2 and 10 kDa; the polylysine of the outer coating is of a molecular weight of between 2 and 10 kDa; the internal particles are geometrically stabilized, as is described below; the composite microreactor is generally stabilized, as is discussed below; the super matrix is free of fissures or other defects which arise from the use of internal particles which have not been geometrically stabilized; the diameter of an internal particle, is between 100 and 400 microns, preferably about 200 microns; the diameter of the composite microreactor is between 400 and 800 microns, preferably about 600 microns.

As described above, the internal particle (20) can consist of sources embedded in a matrix, the matrix being enclosed in an internal particle coating. The internal particle (20) can also have other structures. For example, the inner particle can consist of a solid bead, e.g., a plastic bead, a sepharose bead, or a glass bead, on which cells, e.g., anchorage dependent cells, are allowed to grow. Cells can be allowed to grow on a surface of the solid bead or, if they are present, within interstitial spaces of the bead. Such an internal particle can be coated as described herein, or left uncoated. The internal particle can be coated or left uncoated. The internal particle, can be embedded in a super matrix, the super matrix being enclosed by coating.

Composite microreactors can also contain fibers or materials to enhance the mechanical strength of the sphere. Similarly, the composite material can contain substances such as PEO which may act to repel protein and to hinder the fibrotic response. Other materials such as gelatin or collagen can also be added to either increase or decrease the porosity so as to influence the transport properties (permeability/and or molecular weight cutoff).

In addition to advantages, such as case of retrieval, the embodiments of the invention permits the use of immuno-protectants which are not biocompatible. Materials which alone might be digested by enzymes, or which might trigger a fibrotic response when they come into direct contact with host tissues can be used to form permselective barriers. Methods of the invention can also be used to alginate-coat particles made of neutral or positively-charged substances. More importantly, the alginate coating furnishes the composite structure with a physical barrier of substantial thickness versus the "coating" formed by mere electrostatic interactions. The composite structure (ranging in diameter from <50 μm to >5 mm) can be made of any material.

Internal particles can be of any shape, including, for example, planar, cubical, tubular, and disk-shaped particles and chambers, or other shapes which might otherwise become fibroencapsulated.

The ratios of the volume of the internal particles to the volume of the composite microreactor can be tailored to particular applications, but preferred ratios are 0.5:5.0, preferably 1.0:3.5, more preferably 1.0:2.5, or 1.0:3.0.

Higher Order Composites

Figure 2:
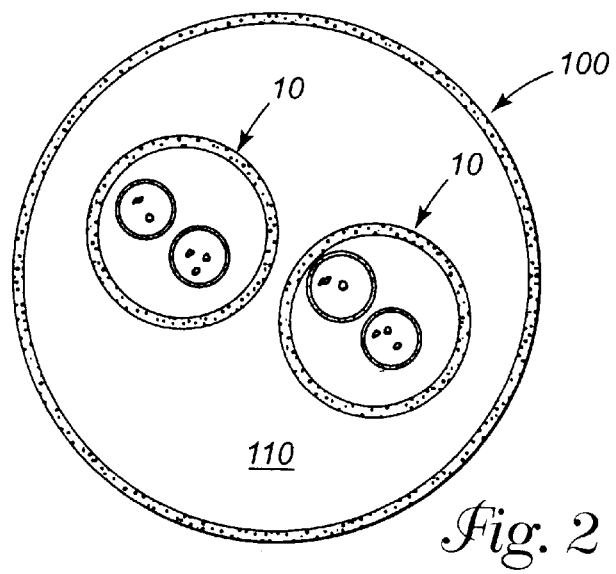

Embodiments of the invention include higher order composite microreactors, e.g., a double composite in which single composite microreactors (10) are embedded in a matrix which is (optionally) coated with an outer coating. Accordingly, FIG. 2, shows a second order, or double composite microreactor (100).

The double composite microreactor (100) contains one or a plurality of composite microreactors (10) (as described above and elsewhere herein) embedded in a double composite microreactor matrix or super matrix (110) which is (optionally) enclosed in a double composite microreactor outer coating (120).

The diameter of the double composite microreactor (100) is preferably between 100 microns and 4 millimeters, between 300 and 1500 microns, between 400 and 1000, or between 500 and 900 microns. More preferably the diameter is about 600–800 microns.

Double composite microreactor matrix or super matrix (110) can be a gel, e.g., a hydrogel, e.g., alginate or agarose. The double composite microreactor matrix or super matrix (110) can have immunoisolative properties. In some embodiments it can have little or no ability to exclude low molecular weight species, e.g., IgG or complement, with this property being relegated to other components of the composite microreactor (10). The double composite microreactor matrix or super matrix (110) can be rendered immunoisolating by controlling its porosity, e.g., such that it hinders the passage of molecules of relatively large molecular weight or by adding to it components, e.g., PEO, PSA, or PLO which hinder the passage of relatively large molecules. Regardless of the method of controlling its permeability, the matrix or super matrix (110) will, in preferred embodiments, hinder the passage, and preferably, essentially completely prevent the passage of molecules having a molecular weight of more than about 50 kDa, preferably more than about 100 kDa, preferably more than about 150 kDa, and most preferably more than about 400 kDa; or of immune system components such as Ig molecules or complement; or recipient-derived cells. The double composite microreactor matrix (110) need not be anti-fibrotic and need not be biocompatible if a more proximal or more exterior component supplies these functions. In double composite microreactors the matrix of the inner most particle is usually referred to as the internal particle matrix. The matrix in which the internal particles are embedded is usually referred to as the particle matrix, and the matrix in which the single composite particles are embedded is usually referred to as the super matrix.

Double composite microreactor outer coating (120) is optional. It can be made of a polyaminoacid, e.g., PLL, PLO, chitosan, or PAN-PVC, or any coating used to coat non-composite microreactors. A preferred coating is a poly amino acid, e.g., polylysine, having a molecular weight of less than 15 kDa, more preferably of less than 10 kDa, more preferably of less than 5 kDa. Particularly preferred are polylysines with a molecular weight of about 3–4 kDa, e.g., 3.7 kDa, or about 9 kDa–10 kDa, e.g., 9.7 kDa. Preferred coatings are volume-reducing coatings. The double composite microreactor outer coating (120) need not be immunoisolating if other components supply this function.

Other embodiments of the invention include higher order composite microreactors, e.g., third order composites which include double composite microreactors embedded in a matrix and (optionally) enclosed in an outer coating, and forth order composites, which includes third order composites embedded in a matrix and (optionally) enclosed in an outer coating. The materials and methods discussed for use in single and double composites can be used for the matrices and coatings of higher order composites.

Isolation of Cells

Living cells can be isolated from surrounding tissues or grown in culture by procedures known to the art, and then suspended in a liquid medium prior to encapsulation. The living cells can provide biological substances, e.g., enzymes or co-factors, hormones, clotting factors, or growth factors. Cells, e.g., pancreatic cells, can provide enzymatic or hormonal functions. Cells such as hepatic cells can provide a detoxification function.

As an example, pancreatic islet cells were prepared from either adult mongrel dogs, pigs, or bovine calves (0–2 weeks old) by a modification of the methods of Warnock and Rajotte, *Diabetes,* 37:467 (1988), as previously described in Lanza et al., *P.N.A.S. USA,* 88:11100–11104 (1991).

Briefly, aseptic, viable porcine pancreata were obtained under aseptic operating room procedures. After resection (warm ischemia for less than about 15 minutes), the glands were cannulated and infused with cold (4° C.) University of Wisconsin (UW) organ preservation solution. Pancreatic tissues were dissociated using an intraductal collagenase digestion procedure. The collagenase is delivered by peristaltic pump, and the digested pancreas is mechanically disrupted in a polypropylene dissociation chamber containing 2–6 mm glass beads. The islets were separated from the exocrine tissue by discontinuous density gradient centrifugation (27%, 20.5%, and 11% (w/v) FICOLL® (Sigma, F 9378) in Eurocollins solution).

Isolated islets were then cultured for one day either in M199/Earle's medium supplemented with 10% (vol/vol) fetal bovine serum, 30 mM HEPES, 100 mg/dl glucose, and 400 IU/ml penicillin (canine), or in α-MEM plus 10% heat-inactivated horse serum (bovine and porcine) in a humidified atmosphere of 5% $CO_2$/95% air at 37° C. A typical yield of islets should be in the range of $0.5–1.8 \times 10^6$ islets for adult pancreas (400 gm wet weight, islet diameter 80–125 μm, purity 85–95%, viability greater than 90% (see below). The cells may also be isolated by other procedures and cultured under other suitable conditions.

Ischemic deterioration of the islet cells is minimized by using tissue fragments of a suitable size, e.g., islet fragments should be less than about 150 microns, and preferably 50 to 125 microns, in diameter. Viability, growth, longevity, and/or function of the islet cells can be enhanced by co-culturing, i.e., by mixing other cell types in the liquid medium prior to encapsulation. Useful cell types include cells which secrete growth hormone, e.g., GH-3 cells, or cells which secrete connective tissue and/or extracellular matrix components, e.g., fibroblasts and endothelial cells. In addition, cells, e.g., islets, can be co-cultured with red blood cells, or hemoglobin, or other oxygen carrying agents can be added, to enhance oxygen availability. Red blood cells can also be used to scavenge nitric oxide.

Islet quality control procedures are used to enable comparison of different lots of islets prepared at different times. Purity (amount of islet tissue compared to exocrine tissue contamination) can be determined by ability of pancreatic islets to rapidly take up diphenyl thiocarbazone (dithizone). Islets can be incubated for five to ten minutes with 50 μg/ml of dithizone (D5130, Sigma) to stain them red. The preparation is then examined under light microscopy for a qualitative estimate of purity. Quantification of purity is effected by islet dispersion and counting of stained and unstained cells, or with a spectrophotometric assay of dithizone uptake/μg DNA.

Viability can be determined by any one of several assays that depend on the capability of viable cells to exclude certain dyes. For example, one assay uses a combination of the fluorescent stains acridine orange, which stains only viable cells green, and propidium iodide, which stains only the nuclei of dead cells red. The islets are incubated with the dyes (acridine orange, Sigma A6014, 50 μg/ml, and propidium iodide, Sigma P4170, 2.5 μg/ml) in a PBS solution for 10 to 15 minutes and then dispersed into single cells. Counts of red and green fluorescing cells are used to calculate % viability.

Insulin secretory activity of the islets is determined both in static culture, e.g., expressed as units of insulin per islet volume, and based on the capability of the islets to respond to graded concentrations of glucose. These values are quantitatively established by measuring the insulin secreted by islets exposed to a range of glucose concentrations extending from 2.8 to 28 mM glucose.

Formation of Microcapsules

Living cells, e.g., islet cells, can be encapsulated in a variety of gels, e.g., alginate, to form microparticles, e.g., microbeads or microspheres to physically isolate the cells once implanted into a host. To prevent entry of smaller molecular weight substances such as antibodies and complement (with a molecular weight of about 150 kDa) into these microparticles, they can be coated with a material such as poly-L-lysine, chitosan, or PAN-PVC, which provides an outer shell with a controlled pore size, or they can be treated by, e.g., cross-linking, to control their internal porosity. Alternatively, their porosity can be controlled by mixing various substances such as polyethylene oxide (PEO) directly into the gel mixture. The use of a high molecular weight molecule, e.g., a high molecular weight PEO, e.g., of about 1–8 million Da, will minimize the escape of the porosity controlling substance. Molecules of this size range can be used with out an outer coating.

Encapsulation

Once the cells are isolated and suspended in liquid medium, they can be encapsulated by a supporting matrix, e.g., a hydrogel matrix to form a microbead, which serves as a core of a microcapsule, e.g., or internal particle. The core maintains a proper cell distribution, provides strength, and enhances cell viability, longevity, and function. The core can also contribute to immunoisolation. For example, the physical distance that is created by embedding the internal particle in a supporting matrix, can provide protection from, e.g., nitric oxide and cytokines. It also protects the internal particle from direct cell-cell interactions which can elicit an undesirable host response.

Using standard techniques, a gel matrix is formed by adding cells, e.g., pancreatic islets, to a solution of nutrient medium and liquefied gel, e.g., sodium alginate, to form a suspension, and then crosslinking the gel. The gel matrix can be any one or a combination of a variety of substances, preferably substances which are biocompatible with the host animal, and arc capable of maintaining cellular viability and physically supporting the tissue or cells in suspension.

The gels can be gelled or crosslinked, e.g., by the addition of ions such as calcium, potassium, or barium, or by a change in temperature. Though, if temperature change is used care should be taken so that the temperature changes required for gelation are not harmful or fatal to the living cells to be encapsulated. Temperature-independent gels include alginates, carrageenans, and gums such as xanthin gum. As used herein, the term alginate includes alginate derivatives. These gels should be treated to remove polyphenols, lipopolysaccharides, endotoxins, and other impurities using standard techniques.

Alginate is composed of blocks of 1,4 linked β-D-mannuronic acid (M) and α-1-guluronic acid (G) linked together, e.g., in alternating MG blocks. The preferred alginate is one formulated with a high G block content, e.g., at least about 60 percent. The higher the percentage of G blocks, the greater the pore size and the strength of the gel matrix. In addition, alginate gels with a high M block content appear to be more immunogenic than gels with a high G block content. See, e.g., Soon-Shiong et al., *Transplant. Proc.,* 23:758–759 (1991), and Soon-Shiong et al., *Transplantation,* 54:769–774 (1992).

The gel matrix should be sufficiently viscous to maintain the cells in a dispersed state. When alginate is used as the gel matrix, it is added up to about 3%, preferably to about 1 to 2%, of the liquid medium, and the solution is cross-linked to form a semisolid gel in which the cells are suspended. These percentages provide a matrix that maintains its shape and has sufficient mechanical strength to remain intact in vivo for several months.

Alginate hydrogels are preferred for the microbead cores of the internal particles for a number of reasons. Alginate allows rapid polymerization and immobilization of cells at room temperature using relatively benign $CaCl_2$, provides consistent gel rheology that can be conveniently varied by increasing alginate concentration, and produces microbeads with good mechanical strength.

In contrast, although agar/agarose has been found to be an excellent medium for embedding isolated porcine, canine, and bovine islets, significant problems were encountered in preliminary studies to embed isolated islets in agar microspheres. Requirements for elevated temperatures and the heterogeneous rheology of agar significantly complicated the procedure. For example, temperatures above the physiologic range irreversibly damaged the islets.

A preferred method for making hydrogel microbeads is with an air jet.

Other methods for making hydrogel microbeads including emulsification, dripping, and the Rayleigh jet.

Emulsification

Emulsification depends upon shear forces in an immiscible liquid to break up the pre-gel liquid. The shear forces are usually produced by agitation although they can be produced by wall shear in a lumen or by sonification. Well controlled agitation can produce droplets which are uniform to about ±15% in diameter, and it is an acceptable technique often used to encapsulate living cells. See, e.g., Lencki et al., U.S. Pat. No. 4,822,534.

Dripping

In this group of related techniques, a force is applied to pre-gel liquid in which living cells are suspended, which overcomes the surface tension force between the forming droplet and the extruding orifice. The orifice may take many forms; frequently a blunt-tipped hypodermic needle is used.

Various forces can be applied to the droplets, e.g., centrifugal, electrostatic, or inertial. A centrifugal force of about 536 g is suitable for use with an extrusion orifice large enough to pass 100 μm islets to produce 200 μm droplets. A suitable rotor to produce microspheres with centrifugal force is a multiorifice centrifugal head, e.g., as described in Deasy (ed.), "Microencapsulation and Related Drug Processes," Chapter 13 (Marcel Dekker, Inc., NY & Basel, 1984) (Southwest Research Institute, San Antonio, Tex.). Another suitable rotor is described in U.S. Pat. No. 4,386,895.

Axial inertial forces, as employed in ink jets which "spit" a single droplet from an orifice by pulsing a pumping chamber with a piezoelectric crystal, or in so-called "bubble" jets which boil microvolumes of fluid to create a pressure pulse, are also suitable for the present invention.

Fluid flow drag is another common method used to form microdroplets in the 200 to 1000 μm size range. In this method, a liquid is extruded steadily from an orifice (usually a hypodermic needle) which is arranged within a coaxial jet of gas. The drag force "shear" of the gas flow, with a velocity of up to 400 m/sec, pulls the forming droplet away from the needle against the retaining force of surface tension. The droplets are typically twice the diameter of the orifice, which makes 400 μm diameter droplets, with less than or equal to 100 μm diameter islets, the smallest practical size using this method.

Rayleigh Jet

The Rayleigh jet can be used to manufacture very uniform (±1%) microdroplets and even encapsulated microdroplets by means of two coaxial jets. This technique is based upon the principle, first illustrated by Lord Rayleigh in 1873, that a liquid jet is inherently unstable against surface tension. Rayleigh demonstrated that there is a particular geometry that produces a characteristic frequency (where f=frequency; V=jet velocity, D=diameter of microdroplet): f=0.419 V/D.

Although the drop-passing frequency is completely determined by the jet velocity, the droplet-forming process is completely independent of the jet velocity. This phenomenon has been used to manufacture microdroplets from 20 $\mu$m to 1000 $\mu$m diameter from liquids ranging in viscosity from 1 to 100,000 cps. The jet is disturbed at the Rayleigh frequency by either natural turbulence or, usually, by driving the plenum supplying the jet with an oscillator, typically a piezoelectric crystal, or by inertial forces arising from vibrating the nozzle transversely or axially. Electrostatic or acoustic excitation of the jet can also be employed.

By employing a coaxial flow of an encapsulating liquid and a coating liquid, coated droplets can be formed. Coextrusion is very attractive as long as the core material does not cause a rapid coagulation of the shell material. When the droplets are to be coated with a rapidly coagulating material such as an acrylic copolymer, a temporary barrier liquid (e.g., vegetable oil or a polymer solvent) should be interposed between the core and coating materials.

Controlling Pore Size of Microparticles

The pore size of the microparticles can be controlled either by applying a semipermeable shell having a particular molecular weight cutoff. This can be effected by applying an "electrostatic" coating, e.g., a coating of a polyamino acid, e.g., polylysine. Pore size can also be controlled by treating the gel matrix of the microparticles themselves to change the pore size of the matrix without any subsequent coating. E.g., the surface of the core can be altered by, e.g., cross-linking, to produce covalently modified gel matrix surface. A coating can be a formed by modifying the structure of the matrix, e.g., the matrix can be cross-linked, e.g., with metal ions, e.g., Ba or Fe ions, or by photo-cross-linking, to form an coating.

As used herein, "molecular weight cutoff" refers to the size of the largest molecule that is not substantially blocked, e.g., by a semipermeable shell or coating surrounding a microsphere or by the gel matrix itself or both. Molecules with a molecular weight above the cutoff are substantially prevented from entering or leaving the particle. The composite microreactor should generally provide a molecular weight cutoff of about 50,000, more preferably about 100,000, more preferably about 150,000, and most preferably about 400,000 daltons. In preferred embodiments, the molecular weight cutoff is sufficient to prevent Ig molecules, e.g., IgG, and complement, from entering and coming into contact with the encapsulated material.

Altering the Pore Size of the Gel Matrix

The pore size of the gel matrix can be altered in several ways. For example, the gel matrix can be altered, e.g., the porosity can be either increased or decreased so as to influence the transport properties, e.g., permeability and/or molecular weight cutoff, by adding, e.g., gelatin, or collagen, or barium, or other ions with the same balance as $Ca^{++}$ ions. Changes in the temperature will also affect the pore size. An increase in the temperature will result in shrinkage of the gel matrix. The addition of compounds, e.g., PEO, to the gel matrix can also result in altered pore size. PLO may act to repel protein and to hinder fibrotic response. In preferred embodiments, PEO of molecular weight greater than 1,000,000 Da, more preferably greater than 4,000,000 Da, and most preferably greater than 8,000,000 Da, is mixed with the gel matrix. PEO of relatively high molecular weight will not diffuse out and thus does not require crosslinking.

Coating

Microcapsules, e.g., the internal particles of a composite microreactor, can be coated or uncoated. The internal particles of a composite microreactor can be coated with any coating used to coat non-composite microreactors. Because the internal particles of a composite microreactor do not generally come into contact with recipient tissue, the outer surface of an internal particle, whether or not coated, need not be anti-fibrotic.

Microbeads, or pre-gel microdroplets, can be coated with a coating of a polymer, e.g., a biocompatible polymer, e.g., an electrostatic coating, e.g., a polyaminoacid, e.g., PLL, or PLO, chitosan, "PEO", polyvinyl acetate ("PVA"), or an acrylic copolymer such as PAN-PVC, which is then solidified to form a shell. Known coating methods can be used for coating materials such as poly-L-lysine or chitosan, but polymers which can have undesirable effects on the encapsulated cells, such as PAN-PVC, present special coating problems described below.

A suitable copolymer is PAN-PVC, which, when solubilized in an organic, polar solvent such as n-methyl-2-pyrrolidone (NMP), dimethylsulfoxide (DMSO), dimethyl formamide (DMF), or dimethyl acetamide (DMAC)(all available from Sigma Chemicals Co., St. Louis, Mo.), is coated onto the microspheres and then precipitated by solvent exchange with water to form a porous membrane with pores that exclude molecules larger than about 80,000–150,000 MW.

The coating thickness is preferably greater than 20 $\mu$m, but less than 100 $\mu$m so as not to compromise the microbead core volume. A preferred geometry is a 300 $\mu$m diameter microbead containing two or three islets encapsulated in a 25 $\mu$m thick acrylic copolymer coating to give an outer diameter ("OD") of 350 $\mu$m. If the OD is increased to 500 $\mu$m, a coating thickness up to 100 $\mu$m can be employed, but a thicker coating generally increases the mass-transfer resistance and decreases the number of cells that can be supported by the surface area of the coating. Therefore, the coating is preferably at least 25 $\mu$m, to give sufficient strength, but as thin as possible to allow rapid mass transfer.

Initial attempts to coat batches of microbeads by dipping them in a PAN-PVC coating solution were less than entirely successful because the solvents required to dissolve PAN-PVC are toxic to cells and the solvent quickly diffuses throughout the microbeads when they are dropped into the coating solution. In addition, the PAN-PVC precipitates and solidifies almost instantaneously in the presence of water, making it almost impossible to prevent the microbeads submerged in the coating solution from sticking to each other.

The problem is that the outer surface of the coating around the microbeads is sticky, because at first only the internal surface of the coating that contacts the microbead, and thus the water in the bead, is solidified. As a result, the beads stick together. The outer surface of the coating will solidify only when exposed to an aqueous solution; but by then all the beads are already stuck together. This is especially a problem with large batches of microbeads.

Thus, PAN-PVC, and other polymers that require the use of toxic solvents, must be coated onto microbeads with methods that generally include the following common features: (1) a very brief contact of the cell-containing pre-gel microdroplets or gelled microbeads with the coating solution to avoid toxic effects; (2) the elimination of any handling of or contact between the microbeads before the coating is solidified; and (3) the coating of large numbers of microbeads in a short period of time and on an individual basis.

In each of the methods described below, the polymer solution, e.g., PAN-PVC, is dissolved in a water-soluble, organic, polar solvent, e.g., NMP, and a small amount of water. The solution is solidified by exposure to water, which dilutes the solvent by counter diffusion of the two liquids, causing a fibrous network to form a porous coating on the surface of the microbeads. By varying the composition of the polymer solution, casting temperature, pre-evaporation of solvent, etc., the molecular exclusion size of the copolymer coating can be varied.

In one method of coating microdroplets or gelled microbeads with PAN-PVC, the microbeads are shot through a free-standing thin film "curtain" of a coating solution created by flowing the solution through a narrow slit in the wall of a tube, over a straight edge, i.e., weir, to form a "waterfall" curtain, or out of a rotating centrifugal cup-like device. Pre-gel microdroplets containing immobilized cells are generated, e.g., by Rayleigh jet as described above, and are shot on a ballistic trajectory to penetrate through the free-standing coating film at velocities of 1 to 40 m/sec. During the penetration they are coated with a thin layer of the polymer solution. In order to enhance complete coating of difficult shell liquids (i.e., liquids that are very viscous and/or have a high surface tension), the microdroplets can be given a spin by injecting vorticity, i.e., a swirl, upstream of the droplet-forming orifice. The coated microbeads are then dropped into an aqueous biocompatible collection medium in which the coating, e.g., PAN-PVC, solidifies by contact with water and the coating solvent diffuses away from the gel core into the surrounding aqueous bath. The excess coating solution is collected, e.g., in a funnel, and recycled.

Since the preferred Rayleigh jet can produce large numbers of microdroplets in a short period of time. The microbeads pass through the film one-by-one, so they are all coated on an individual basis. Since the total "in-flight" time before they drop in the collection medium is only a few milliseconds, toxicity of the organic solvents does not play a role. All microbeads remain separate at all times until the outside of the coating is solidified and thus no longer sticky, and are not handled physically. As a result, the sticking/agglomeration phenomenon described above is avoided.

After penetration, coating, and time to regain a spherical shape, the coated microcapsules fall into an aqueous solution that solidifies the shell coating. Ions, e.g., $Ca^{++}$, for crosslinking the ionic gel core, e.g., sodium alginate, diffuse through the shell during and after solvent exchange. The coating film, e.g., from a centrifugal cup, can be 5 to 50 $\mu$m thick depending upon the feed rate, the centrifugal acceleration at the cup lip, and fluid properties, i.e., viscosity, density, and surface tension. If the shell polymer solidifies too rapidly on the gel microbeads, they may be frozen at their surfaces by liquid nitrogen or its vapor.

This method of curtain coating can also be used for other applications in which only the surface of a small particle, such as a gel microbead or pre-gel droplet, is exposed to a solution that is used to change the surface characteristics of the microbead or droplet. For example, a curtain solution of $BaCl_2$ can be used to selectively gel only the surface of sodium alginate microdroplets to form a gel surface layer that is denser than the gel formed inside the microdroplet when the droplet is subsequently immersed in $CaCl_2$. If the microdroplets were immersed in a $BaCl_2$ solution, the entire microdroplet would be gelled to the same density which probably would harm the living cells because the pore size could be too small to give them adequate space.

Coating with Polylysine

To coat an alginate core with polylysine the alginate core is dropped into a solution of 0.05% polylysine in serum free culture medium. The thickness of the polylysine coating can be increased by increasing the time the alginate core is left in the solution, or alternatively, by increasing the concentration of the solution. The volume of beads to solution can be, e.g., 1:5, 1:10, or 1:20. For smaller beads a greater proportion of solution is desirable.

Coatings Which Minimize Particle Volume

Embodiments of the invention use coatings which reduce the volume of a component, e.g., a core, to which they are applied. For example, a polyaminoacid coating, e.g., a polylysine, or polyornithine made from a polyaminoacid of a relatively low molecular weight, can result in a significant reduction in the volume of a gel core, e.g., an alginate core, to which it is applied. In many cases the reduction in volume is as much as about 50%, or even 60–70%, or more.

Relatively low molecular weight, as used herein, means about 30,000 Da or less, more preferably about 15,000 Da or less, more preferably about 10,000 Da or less, more preferably about 8,000 Da or less, more preferably about 7,000 Da or less, more preferably about 5,000 Da or less, more preferably about 4,000 Da or less, more preferably about 3,000 Da or less, and most preferably about 1,500 mDa or less.

For example, the use of polylysine of a relatively low molecular weight, e.g., 3.7, or 9.6 kDa, can result in a significant reduction, (approximately 30% in some cases) in the diameter, of the core to which it is applied. In addition to the decrease in volume, the use of a low molecular weight polyaminoacid will result in a coat having superior permselective properties. However, the use of a low molecular weight polyaminoacid often results in a surface which is "pruned", i.e., relatively convoluted or rough, and which can elicit a fibrotic response. The composite microreactor of the invention, by using this coating on the internal particle, and a smooth surface, e.g., of alginate, on the exterior of the composite microreactor, can obtain the benefits of a coating of relatively low molecular weight and also inhibit fibrosis.

The permselectivity properties of a poly amino acid, e.g., a polylysine, coating improve after the coating has been aged 2 or more hours. Thus, for best results, particles coated with these coatings should not be implanted in recipients until the coating has aged.

Geometric Stabilization

Some particles or components are not geometrically stable immediately after manufacture, e.g., the particle or component can change size or shape. If internal particles which are incorporated into a composite microreactor change geometry, the components of the composite microreactor, e.g., the super matrix or outer coating, can be damaged and the integrity of the composite microreactor can be compromised. Although not wishing to be bound by theory, the inventors believe that changes in the geometry may damage the super matrix or the outer coating, e.g., by inducing fissures or discontinuities. Damaged particles can allow the fibrotic proliferation of recipient cells on the inner particles when implanted into a recipient. Therefore, it is often desirable to geometrically stabilize internal particles, preferably prior to incorporating them into composite microreactors. Stabilization can generally be accomplished by allowing the particles to "age" for a short time before incorporation into larger structures. The aging should be done under condition which maximizes the viability of encapsulated cells. Geometric stabilization is particularly important when the particles are coated with a relatively low molecular weight poly-amino acid.

Polylysine-coated alginate particles, especially those coated with relatively low molecular weight polylysine, should be geometrically stabilized. The polylysine coated alginate particles should be placed in a culture medium, suitable for the cells being used, and allowed to stabilize overnight.

Formation of Composite Microreactors

Composite microreactors can be made by materials which are analogous with the methods used to make internal particles: individual or small numbers of internal particles (rather than cells) are embedded in a matrix (referred to herein as a super matrix to distinguish it from the internal particles matrix) and an (optional) outer coating applied.

For example, after the internal particles are prepared and, e.g., either coated or otherwise treated, e.g., cross-linked, they should be washed in medium to prevent the existing microparticles from sticking to each other (particles that have not been coated should be washed in calcium and magnesium free medium), mixed with a liquid hydrogel such as alginate, and formed into a composite microparticle with a diameter from less than 50 μm up to more than 5 mm. For example, in a method which is analogous to that described above for the creation of the internal particles, a mixture of internal particles in a liquid gel can be extruded through an 18 gauge catheter to form composite microreactors.

As is discussed elsewhere herein, it may be desirable to geometrically stabilize the internal particles before incorporating them into a composite microreactor.

The super matrix of a composite microreactor can provide a semipermeable shell of a hydrogel material around all of the encompassed internal particles that can provide a physical barrier of substantial thickness compared to the individual coatings on each of the microcapsules. Electrostatic interactions in the super matrix can contribute to immunoisolation.

The super matrix can be made of the same material as the internal particle matrix or it can differ from the matrices of some or all of the internal particle matrices.

A composite microreactor can contain internal particles of any shape, including, for example, planar, cubical, tubular, and disk-shaped particles and chambers, which might otherwise become fibroencapsulated.

A composite microreactor can also contain other substances to modify the properties of the composite microreactor and can, e.g., include fibers or materials in addition to the hydrogel matrix and internal particles to enhance the mechanical strength of the composite microreactor. Similarly, the composite microreactors and particularly the super matrix, can include substances such as PEO which act to repel proteins and to hinder the fibrotic response. Other materials such as gelatin or collagen can also be added to the super matrix to either increase or decrease the porosity so as to influence the transport properties (permeability and/or molecular weight cutoff) of the composite microreactors.

Higher order composites can be made by analogous methods.

Outer Coating

Composite microreactors can (optionally) be provided with an outer coating. Although any coating used with non-composite microreactors or for internal particles can be used for the outer coating, other coatings, or no coating, can be used as well. Because the various properties needed by the implanted device, e.g., biocompatibility, the ability to resist fibrotic encapsulation, the ability to prevent recipient immune inactivation of the implanted donor tissue, can be distributed among the various components of the composite microreactor, the outer coating need not supply all of these properties. It may be desirable to geometrically stabilize the supermatrix prior to application of a coating.

Implantation

The composite microreactors can be implanted into a host by injection with a standard catheter or syringe, e.g., with a 16 gauge needle for beads less than 1000 μm in diameter. Larger composite microreactors can be inserted via a small incision, e.g., with a catheter or funnel-like device. The beads are preferably implanted into the host intraperitoneally. The beads can also be implanted intramuscularly or subcutaneously. Alternatively, the beads can also be implanted into immunoprivileged sites such as the brain, testes, or thymus, where the host's immune response is least vigorous, as described in Chapter 7 of Lanza et al. (eds.), *Immunomodulation of Pancreatic Islets* (RG Landes, Tex., 1994). Composite microreactors can also be introduced at a site where the substance provided by the composite microreactor is needed locally. E.g., a microcapsule which provides α-interferon could be implanted in tumors. The microreactors of the invention can be delivered to a subcutaneous site. The composite microreactors can be inserted through a small surgically created opening using a gun/trocar type device that slips the beads under the skin.

EXAMPLE 1

Encapsulation of Pancreatic Islets

Pancreatic islets were encapsulated as follows. After preculturing overnight, islet cells were suspended uniformly at a density of 30,000 islets/ml, which is 30 islets/mm$^3$, in a solution of 1.5% (wt/vol) Pronova LVG sodium alginate (Protan, Drammen, Norway) in culture medium plus additives (α-MEM, 10 mM HEPES pH 7.1, penicillin, 2 mM glutamine for porcine islets; and M199 with the same additives for canine islets). A syringe pump was used to pump the suspension through an air jet apparatus (containing a straight-edged 22 gauge needle) at a speed of 3 ml/min. Droplets formed at the tip of the needle were stripped off by means of a concentric flow of air at an air speed of 7 to 8 m/sec. The resulting droplets fell a distance of 4 cm and were collected in a solution of 1.5% $CaCl_2$ in 10 mM HEPES (pH 7.1) to form gelled beads. These beads can be made in various sizes ranging from about 100 μm to 400 μm in diameter by altering the air flow speed, the faster the flow rate the smaller the beads.

Each bead contains approximately 1 to 2 islets. After gelation, the beads were washed three times with culture medium (appropriate for the species of islets in use), and were then cultured in a tissue culture incubator at 37° C. and 5% $CO_2$ until implantation.

Larger beads up to 3 mm in diameter can be made in a similar manner, or can be extruded through a syringe with a 18 gauge catheter.

EXAMPLE 2

Formation of Composite Microreactors

Composite microreactors are made as follows:

Step: 1: Day 0. A mixture of islets and sodium alginate (30,000 islets/ml) are extruded with a droplet generation device (an airjet with a 22 gauge needle) into a 1.5% $CaCl_2$/10 mM HEPES solution. The apparatus is run on atomization mode to generate minispheres approximately 300 μm in diameter. The gelated spheres are collected and washed in culture media several times. Generally the gelated spheres are aged for about 24 hours before proceeding to Step 2.

Step: 2: Day 1. The minispheres are washed in serum free media several times and coated with polylysine by immersion in a solution of 0.2% 9.6K (or 5-less than 15 kDa) polylysine (or 3.7K (or 1 kDa–4 kDa polylysine)) for 2 minutes. The spheres are then washed in complete culture media (i.e. media containing serum).

Step: 3: Day 2. There is usually a 3–5 day aging period between Step 2 and the beginning of Step 3 when 1 kDa–4 kDa polylysine is used. Otherwise the outer composite matrix can develop cracks which could allow host cell penetration. There is usually a 24 hour aging period between Step 2 and the beginning of Step 3 when 5 kDa-less than about 15 kDa polylysine is used. The polylysine-coated minispheres are mixed with sodium alginate (the ratio of settled bead volume to alginate is 1:3). The mixture is run through the airjet using a 20 gauge needle to generate spheres approximately 600 μm in diameter if single composites are to be made. The mixture is run through the airjet using an 18 gauge needle to generate spheres approximately 900 μm (or larger) in diameter if double composites are to be made.

The above recited protocol results in composite microreactors, these can be used as is to deliver islets to a host, coated with an outer coating and used to deliver islets to a host, or used to make higher order composites to deliver islets to a host.

EXAMPLE 3
Formation of Double Composite Microreactors

Double composites are made as follows:

Perform steps 1–3 as described in Example 2 above.

Step 4: Day 3. There is usually an aging period of about 24 hours between Step 3 and Step 4. Wash and coat composite spheres with polylysine as described in step 2 in Example 2.

Step 5: Day 4. There is usually an aging period of about 24 hours between Step 4 and Step 5. The polylysine-coated composite spheres are mixed with sodium alginate (ratio 1:3 as above). The mixture is run through the airjet using an 18 g needle to generate spheres approximately 900 μm in diameter.

The above recited protocol results in double composite microreactors, these can be used as is to deliver islets to a host, coated with an outer coating and used to deliver islets to a host, or used to make higher order composites to deliver islets to a host.

EXAMPLE 4
In Vitro Testing of Composite Microreactors

FIG. 3 shows the in vitro insulin output of bovine islets encapsulated using composite microreactors (made as described in Example 2). The microreactors maintained excellent secretory function, averaging 144±11 uU/EIN/day during the first six weeks. The ability of these microreactors to maintain activity during long-term culture show they can provide an in vitro implant with reasonable longevity.

In addition to demonstrating long-term islet viability and function, in vitro studies were also carried out to test the insulin secretory activity from the islets seeded in the microreactors and to evaluate the kinetic performance of the composite microreactors. An approximately four- to fivefold increase from the basal insulin secretion was observed. The secretory response of the encapsulated islets was sustained for one hour of glucose stimulation (300 mg/dl) and returned to basal levels after perfusion with the low-glucose solution (50 mg/dl). A second glucose challenge resulted in a similar insulin secretory response with virtually no delay before the insulin concentration in the perifusate began to increase. These finding show that islets encapsulated by this procedure can respond in a physiological fashion to fluctuations in concentrations of glucose.

EXAMPLE 5
Introduction of Composite Microreactors into Diabetic Rats

Experiments in streptozotocin-induced diabetic rats clearly demonstrate the advantages of composite microreactors of the invention. When non-immunosuppressed diabetic rats received either bovine or porcine islets encapsulated using the standard PLL-alginate procedure cited in the literature (see e.g., *Immunomodulation of Pancreatic Islets* (RG Landes, Tex., 1994) the animals became hyperglycemic in <4 days. The addition of CsA therapy (20–30 mg/kg/day s.c.) prevented this primary nonfunction. However, by 12 to 16 days postimplantation the implants failed despite the immunosuppressive therapy. In contrast, when STZ-induced diabetic rats received bovine islets encapsulated using composite microreactors (made as described in Example 2)the implants continued to maintain prolonged function without the use of any immunosuppressive therapy. In one set of experiments, seven rats received bovine islet grafts ($2\times10^5$ islet equivalents [EIN]) encapsulated in composite microreactors. Nonfasting plasma glucose concentrations promptly dropped from a preimplantation value of 375±25 to 99±21 mg/dl (mean±SEM) during the first week. Three of the animals were sacrificed with functioning grafts 3 to 4 weeks postimplantation. The remaining animals sustained normoglycemia for >8 weeks. Immunohistochemical staining of the explanted microreactors revealed multiple, viable, insulin-containing β-cells consistent with functionally active hormone synthesis and secretion; the external surfaces of the microreactors were free of fibrotic overgrowth and exhibited only occasional host cell adherence. To test further the secretory function of the bovine islets, microreactors recovered two months after implantation were incubated in medium containing either basal (2.8 mM [50 mg/dl] or stimulatory (16.8 mM [300 mg/dl]) concentrations of glucose for 24 hours. In three separate experiments in which this test was performed, the islets responded with an approximately one-to three-fold increase above basal insulin secretion. In contrast, few or no bovine islets survived when immobilized in uncoated alginate microspheres and implanted into the peritoneal cavity of five non-immunosuppressed rats for 9 to 14 days. In other studies, loss of blood glucose control and histology confirmed that the islets immobilized inside these uncoated alginate microspheres were rejected within approximately one to two weeks after implantation.

EXAMPLE 6
Introduction of Composite Microreactors into Normal Dogs

Composite microreactors have also been used to prevent immune rejection of discordant bovine islet xenografts in dogs (made as described in Example 3). The islets were immobilized in composite microreactors and implanted into the peritoneal cavity of adult mongrel dogs both with and without immunosuppression. In a preliminary set of experiments in dogs (n=5), bovine islets were implanted in either uncoated, IgG- and complement-permeable, alginate spheres or in composite microreactors for 3–4 weeks. No islets survived in the uncoated alginate microspheres—even with the use of immunosuppressive therapy (CsA, 10 mg/kg/day). However, when the islets were immobilized within the composite microreactors, viable tissue was observed both with and without immunosuppression. Immunohistochemical staining revealed well-granulated β-cells and indicated that the microreactors excluded canine IgG. Explanted islets responded to glucose stimulation with an approximately three to six fold average increase above basal insulin secretion. These results indicate that survival of discordant xenografts can be achieved in both rodents and dogs without immunosuppression.

OTHER EMBODIMENTS

The composite microreactors of the invention can be used to treat a variety of disorders. These include disorders that result from the defective or insufficient production of a particular substance, e.g., enzyme or hormone, and other disorders, e.g., trauma-related disorders, such as spinal cord injury.

A number of well-characterized disorders caused by the loss or malfunction of specific cells in the body are amenable to composite microreactor-medicated replacement therapy. For example, in addition to the use of islets of Langerhans, which can be used for the treatment of diabetes as is described above, hepatocytes can be used for the treatment of hepatic failure, adrenal gland cells can be used for the treatment of Parkinson's disease, cells that produce nerve growth factor (NGF) can be used for the treatment of Alzheimer's disease, cells that produce factors VIII and IX can be used for the treatment of hemophilia, and endocrine cells can be used for the treatment of disorders resulting from hormone deficiency, e.g., hypoparathyroidism.

Moreover, by using recombinant DNA methods to supply a cell which produces a disease product, or encapsulating other tissues, composite microreactors can be used to treat patients suffering from chronic pain, cancer (e.g., hairy cell leukemia, melanoma, and renal carcinoma), AIDS (treated by immunological augmentation), Kaposi's Sarcoma (treated by administration of interferon, IL-2, or TNF-α), primary hematologic disorders, patients with long-lasting aplasia, and patients who are myelosuppressed (treated by bone marrow transplantation and aggressive chemotherapy). Composite microreactors should also be useful in the treatment of affective disorders, e.g., Huntington's Disease, Duchenne's Muscular Dystrophy, epilepsy, infertility. Composite microreactors can also be used to promote wound healing and to treat traumatic, mechanical, chemical, or thermal injuries, e.g., spinal cord injuries, and in wound healing.

Implantation of specific cells can also serve to detoxify, modify, or remove substances from the circulation, e.g., drugs, poisons, or toxins. For example, the implantation of appropriate living cells restores normal physiologic function by providing replacement for the diseased cells, tissues, or organs, e.g., in hepatic encephalopathy (produced by liver disease) or uremia (produced by kidney failure).

In embodiments of the invention, the encapsulated cells can release fairly large molecules, e.g., IgG molecules. In many applications the critical host component which must be excluded is Clq, which has a molecular weight of about 410 kDa. Thus, the molecular weight cutoff will be about 400 kDa and molecules of up to this size can be released. Genetically engineered cells can also be used in the methods of the invention. For example, cells can be engineered to release larger products, e.g., IgG.

In each application, a sufficient number of composite microreactors, containing the desired living cells, can be implanted into the patient, e.g., surgically or with a syringe. The composite microreactors are implanted, e.g., intraperitoneally, for a systemic effect, or into a particular location, e.g., the brain to treat Parkinson's disease, or the spinal cord to chronic pain or treat spinal cord injuries, for a local effect.

The dose of composite microreactors to be used is determined initially from results of in vitro studies. In addition, in vivo results in, e.g., mice, rats, or dogs will facilitate more accurate assessment of required doses, as these tests are generally predictive of efficacy in human patients. For example, canine insulin dependent diabetes represents an excellent model of cellular and humoral autoimmunity (Nelson, *Diabetes Spectrum* 5:324–371 (1992))

The composite microreactors are intended to remain in the patient with viable donor cells for extended periods of time up to several months or years. However, if it is determined that the donor cells are no longer viable, e.g., by monitoring the patient's blood for a certain level of the protein secreted by the donor cells, it is a simple task to remove the composite microreactors and renew the supply of beads in the patient.

Diabetes Mellitus

To treat diabetes, e.g., in a dog or human patient, the implantable beads preferably encapsulate isolated canine or porcine islets or other cells that produce insulin or insulin-like growth factor 1 (IGF-1). Islets are prepared and encapsulated using procedures described above. Insulin secretory activity of the encapsulated cells or islets is determined both in static culture, e.g., expressed per islet volume, and based on the capability of the islets to respond to graded concentrations of glucose. These values are established as described above. Once the insulin secretion activity of a particular batch of encapsulated islets is determined, the proper number of beads can be determined and implanted into a diabetic patient. For example, to treat a human patient that requires 20 to 50 units of insulin per day, the total number of beads should be selected to contain a total of about 1.0 to 2.5 million porcine islets. For beads designed to contain, on average, 30,000 islets/ml of gel, the proper dosage would be beads made from 30 to 85 ml of gel.

Hemophilia Hemophilia is an X-linked hereditary bleeding disorder caused by Factor VIII or Factor IX deficiency. Recombinant methods have now been successfully used to create Factor VIII- and Factor IX-producing cells as described above. Encapsulation in composite microreactors and implantation of such cells according to the present invention can thus be used for an improved treatment for hemophilia.

Hepatic Diseases

Hepatocyte transplantation is useful not only for irreversible hepatic failure, but for several disease processes including hereditary enzyme abnormalities, acute hepatic failure, where the ability of the liver to regenerate may still exist, and as a bridge to whole liver transplantation in patients who develop sudden hepatic failure, either because of medical progression or because of rejection-related complications.

Wong and Chang, *Biomat. Art. Cells Art. Org.*, 16:731 (1988), have demonstrated the viability and regeneration of microencapsulated rat hepatocytes implanted into mice. Viable hepatocytes were microencapsulated in alginate-poly-(L-lysine) and implanted intraperitoneally into normal and galactosamine-induced liver failure mice. Eight days after implantation in the mice with induced liver failure, the viability of the encapsulated rat hepatocytes increased from 42% to nearly 100%. After 29 days, the viability of the encapsulated hepatocytes implanted in normal mice also increased from 42% to nearly 100%. By contrast, free rat hepatocytes implanted into mice all died within four or five days after xenotransplantation. The composite microreactors of the invention are well-suited to treat hepatic failure.

Other investigators have shown that microencapsulated hepatocytes continue the synthesis and secretion of many specific proteins and enzymes. Cai et al., *Hepatology*, 10:855 (1989), developed and evaluated a system of microencapsulation of primary rat hepatocytes. Urea formation, prothrombin and cholinesterase activity, the incorporation of tritiated leucine into intracellular proteins, and the immunolocation of synthesized albumin were monitored in culture. Despite gradual decreases in some of these activities, the encapsulated hepatocytes continued to function throughout the 35-day observation period. In addition, Bruni and Chang, *Biomat. Art. Cells Art. Org.* 17:403 (1989),demonstrated the use of microencapsulated hepatocytes to lower bilirubin levels in hyperbilirubinemia. Microencapsulated hepatocytes were injected into the peritoneal cavity of Grunn rats. Bilirubin dropped from 14 mg/100 ml to 6 mg/100 ml, and remained depressed after 90 days. Again, the composite microreactors of the invention can be used as described above to treat these hepatic diseases.

Parkinson's Disease

Parkinson's disease is a neuronal system disease, involving a degeneration of the nigrostriatal dopaminergic system. Experimental work in both rodents and nonhuman primates has shown that transplantation of fetal tissue containing substantia nigra (dopaminergic) neurons from ventral mesencephalon to dopamine-depleted striatum reinstates near-normal dopamine internalvation and reduces motor abnormalities. In addition, implantation of adrenal chromaffin cells has been shown to reverse chemically-induced Parkinson's disease in rodents.

Widner et al., *Transplant. Proc.*, 23:793 (1991), reported evidence of fetal nigral allograft survival and function up to 10 months after transplantation and immunosuppression (cyclosporine, azathioprine, and prednisone) in a human Parkinson's patient. Beginning from the second month after the transplantation, they observed a progressive decrease in limb rigidity, increased movement speed in a number of arm, hand, and foot movements, and prolonged "on" periods (>80% increase) after a single dose of L-dopa.

Thus, transplantation of fetal neural tissue, or cells genetically engineered to produce dopamine and nerve growth factors or other neurotropic factors, should have a great potential as a new therapeutic approach in patients with neurological disorders. However, in the case of transplanted xenogeneic donor tissue, rejection would pose a serious problem, even by the combined approach of using an immunoprivileged site and by employing immunosuppressive drugs. Therefore the composite microreactors of the invention permit a novel approach to this problem, i.e., the delivery of dopamine for the treatment of Parkinson's disease using encapsulated donor tissue harvested from animals or genetically engineered cells.

Alzheimer's Disease

An estimated 2.5 to 3.0 million Americans are afflicted with Alzheimer's disease. The disease is characterized by a progressive loss of cognitive function associated with degeneration of basal forebrain cholinergic neurons. Studies in animals indicate that Nerve Growth Factor (NGF), e.g., brain-derived neurotrophic factor (BDNF) and neurotrophin-3 (NT-3), available from Regeneron and Amgen, respectively, and other neurotropic factors normally act to support the viability and function of these neuron cells, and that continuous infusion of NGF into the ventricles can prevent injury-induced degeneration of cholinergic neurons as described in Williams et al., *P.N.A.S. USA*, 83:9231 (1986). This treatment correlates with improved cognitive function in rodents with memory impairment as described in Fisher et al., *Neurobiol. Aging*, 10:89 (1989).

These studies suggest that composite microreactors containing grafts of recombinant or natural NGF-secreting tissue such as astroglial cells or developing skin, can be used to treat patients suffering from Alzheimer's disease.

Gene Therapy

Gene therapy is an approach to treating a broad range of diseases by delivering therapeutic genes directly into the human body. Diseases that can potentially be cured by gene therapy include diseases associated with the aging population such as cancer, heart disease, Alzheimer's disease, high blood pressure, atherosclerosis and arthritis; viral infectious diseases such as acquired immune deficiency syndrome (AIDS) and herpes; and inherited diseases such as diabetes, hemophilia, cystic fibrosis, and muscular dystrophy.

In one particular example, a favored approach for human gene therapy involves the transplantation of genetically-altered cells into patients, e.g., as described Rosenberg, et al., *New Eng. J. Med.*, 323:570–578 (1988). This approach requires the surgical removal of cells from each patient to isolate target cells from nontarget cells. Genes are introduced into these cells via viral vectors or other means, followed by transplantation of the genetically altered cells back into the patient. Although this approach is useful for purposes such as enzyme replacement therapy (for example, for transplantation into a patient of cells that secrete a hormone that diseased cells can no longer secrete), transplantation strategies are less likely to be suitable for treating diseases such as cystic fibrosis or cancer, where the diseased cells themselves must be corrected. Other problems commonly encountered with this approach include technical problems, including inefficient transduction of stem cells, low expression of the transgene, and growth of cells in tissue culture which may select for cells that are predisposed to cancer.

The composite microreactors of the invention are well suited to avoid these problems, because they allow the use of standard human cell lines of, e.g., fibroblast cells, epithelial cells such as HeLa cells, and hepatoma cells such as HepG2, as the implanted cells, rather than requiring the surgical removal of cells from the patient. These cell lines are genetically altered as required by standard techniques and are encapsulated and implanted into the patient. These cell lines are much easier to obtain, culture, and work with than individual patients' cells. Moreover, since the composite microreactors prevent the patient's immune system from recognizing and attacking the implanted cells, any human cell lines can be used, making the technique of gene therapy more universally applicable.

Hypoparathyroidism

Acute and chronic symptoms of hypoparathyroidism result from untreated hypocalcemia, and are shared by both hereditary and acquired hypoparathyroidism. The hereditary form typically occurs as an isolated entity without other endocrine or dermatologic manifestations or, more typically, in association with other abnormalities such as defective development of the thymus or failure of other endocrine organs such as the thyroid or ovary. Acquired hypoparathyroidism is usually the result of inadvertent surgical removal of all the parathyroid glands, and is a problem in patients undergoing operations secondary to parathyroid adenoma or hyperplasia. Hypoparathyroidism has been treated in hypocalcemic rats by the administration of microencapsulated parathyroid cells that served as a bioartificial parathyroid. Parathyroid cells can also be encapsulated in the composite microreactors of the invention for use in administration to animal and human patients.

Osteoporosis

The term osteoporosis covers diseases of diverse etiology that cause a reduction in the mass of bone per unit volume. These diseases can be treated by the administration of composite microreactors containing cells that secrete insulin-like growth factor (IGF-1), estrogen in postmenopausal woman to reduce the negative calcium balance and decrease urinary hydroxyproline, androgens in the treatment of osteoporotic men with gonadal deficiency, or calcitonin for use in established osteoporosis.

Reproductive Disorders

There are numerous disorders of the ovary and female reproductive tract that can be treated with progestrogens, estrogens, and other hormones. These include progestrogen, e.g., progesterone, therapy to inhibit pituitary gonadotropins (precocious puberty in girls), and for prophylaxis to prevent hyperplasia in PCOD. Estrogen therapy is used in the treatment of gonadal failure, control of fertility, and in the management of dysfunctional uterine bleeding. Androgens, gonadotropins, and other hormones are used to treat disorders of the testis, e.g., androgen therapy in hypogonadal men, or gonadotropins to establish or restore fertility in patients with gonadotropin deficiency. Accordingly, these diseases can be treated with composite microreactors containing the appropriate hormone-producing cells.

Huntington's Disease

Huntington's disease is characterized by a combination of choreoathetotic movements and progressive dementia usually beginning in midadult life. Distinctive for the disease is atrophy of the caudate nucleus and, to a lesser extent, other structures of the basal ganglia (putamen and globus pallidus). Rodent cells that secrete neurotropic factors have been implanted into the brains of baboons that have a condition similar to Huntington's disease and reversed some of the damaged nerve networks that, in Huntington's patients, lead to progressive loss of control over the body. Similarly, Huntington's disease in human patients can be treated by the administration of composite microreactors that contain human or recombinant cells that secrete the appropriate neurotrophic factors.

Spinal Cord Injuries

The majority of spinal cord injuries result from damage to the surrounding vertebral column, from fracture, dislocation, or both. Treatment of such injuries involves the administration of nerve growth factors such as ciliary neurotropic factor (CNTF), insulin-like growth factor (IGF-1), and neurotropic factors, to enhance the repair of the central and peripheral nervous system. Thus, composite microreactors containing cells that secrete such factors, either naturally or through genetic engineering, can be used to treat spinal cord injuries.

Mood (or Affective) Disorders

Mood disorders are a group of mental disorders such as schizophrenia characterized by extreme exaggerations and disturbances of mood and affect associated with physiologic (vegetative), cognitive, and psychomotor dysfunctions. Many mood disorders are associated with medical diseases that can be treated with composite microreactors containing the appropriate cells such as hypothyroidism, Parkinson's disease, Alzheimer's disease, and malignancies as discussed herein. In addition, it has been shown that the neurotransmitter 5-hydroxyindol acetic acid (5-HIAA), a serotonin metabolite, is reduced in the cerebral spinal fluid of depressed patients. Deficits in other neurotransmitters such as dopamine and gamma-aminobutyric acid (GABA) have also been identified in patients with major depression. Therefore, composite microreactors containing cells that secrete these neurotransmitter are useful to treat these deficiencies.

Motor Neuron Diseases

Degenerative motor neuron diseases include ALS (see below), heritable motor neuron diseases (spinal muscular atrophy (SMA), and those associated with other degenerative disorders such as olivopontocerebellar atrophies and peroneal muscular atrophy. These diseases can be treated by administration of composite microreactors containing cells that secrete neurotropic factors like brain-derived neurotrophic factor (BDNF), and neurotrophin-3 (NT-3).

Acquired Immunodeficiency Syndrome (AIDS)

AIDS is caused by an underlying defect in cell-mediated immunity due to the human immunodeficiency virus (HIV), and causes persistent constitutional symptoms and/or diseases such as secondary infections, neoplasms, and neurologic disease. Patients can be treated to ameliorate symptoms by immunologic augmentation with composite microreactors that contain cells genetically engineered to secrete, e.g., recombinant human IL-2 (to decrease suppressor cell activity resulting in an increased T cell adjuvant activity); or recombinant human INF-(macrophage augmentation). AIDS-related tumors such as Kaposi's sarcoma can be treated with encapsulated cells that secrete human interferon-$\alpha$, interleukin-2 and tumor necrosis factor (TNF).

Amyotrophic Lateral Sclerosis (Lou Gehrig's Disease)

ALS is the most frequently encountered form of progressive motor neuron disease, and is characterized by progressive loss of motor neurons, both in the cerebral cortex and in the anterior horns of the spinal cord, together with their homologs in motor nuclei of the brainstem. ALS can be treated with composite microreactors that contain cells that secrete nerve growth factors such as myotrophin, insulin-like growth factor (IGF-1), ciliary neurotropic factor (CNTF), brain-derived neurotrophic factor (BDNF) and neurotrophin-3 (NT-3). Animal studies with these factors (IGF-1 is available from Cephalon, CNTF from Regeneron, and NT-3 from Amgen), have demonstrated that they can stem the degenerative effects caused by nerve damage or disease.

Cancer

In most cases, cancer originates from a single stem cell which proliferates to form a clone of malignant cells. Growth is not properly regulated by the normal biochemical and physical influences in the environment. There is also a lack of normal, coordinated cell differentiation. Cancer cells develop the capacity for discontinuous growth and dissemination to other parts of the body.

Various cancers can be treated according to the invention by the administration of composite microreactors containing cells that secrete interferon-a (IFN-$\alpha$) (for solid tumors, hairy cell leukemia, Kaposi's sarcoma, osteosarcoma, and various lymphomas); recombinant interleukin-2 (IL-2) (for melanoma, renal carcinoma, and Kaposi's sarcoma); tumor necrosis factor (IL-2 for Kaposi's sarcoma); recombinant human IFN-$\alpha$ and recombinant human colony stimulating factor-granulocyte macrophage (CSF-gm) (for Kaposi's sarcoma); recombinant human INF-γ (for macrophage augmentation); CSF (for aggressive chemotherapy, bone marrow transplantation, priming of leukemic cells to enhance sensitivity to chemotherapy and to support dose intensification); ciliary neurotropic factor (CNTF) and insulin-like growth factor (IGF-1) (for peripheral neuropathies caused by chemotherapy); adrenal gland cells (for pain relief when injected into the lower spine to secrete natural painkillers) and progestrogen-producing cells (for palliation in endometrial and breast carcinoma).

Duchenne's Muscular Dystrophy

Duchenne's dystrophy is an X-linked recessive disorder characterized by progressive weakness of girdle muscles, inability to walk after age 12, kyphoscoliosis (curvature of the spine), and respiratory failure after the fourth decade. This disease can be treated by administration of composite microreactors containing myoblast cells and growth factors. Myoblasts have been injected into young boys with Duchenne's muscular dystrophy to determine whether the cells can supply a structural protein that is missing. Researchers have observed muscle strength improvement in several of the boys.

Epilepsy

The epilepsies are a group of disorders characterized by chronic, recurrent, paroxysmal changes in neurologic function caused by abnormalities in the electrical activity of the brain. In some forms of focal epilepsy, inhibitory interneurons appear to be preferentially lost. Treatment with neurotropic factors and other neuropeptides such as has been found effective. Therefore, the composite microreactors of the invention containing cells secreting these factors can be used to treat epilepsy.

It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

What is claimed is:

1. A method of making a microcapsule having reduced volume comprising:
   (a) forming a component of a microcapsule, wherein said component is a gel particle; and
   (b) applying a volume reducing coating of a polyamino acid of 15,000 daltons or less in molecular weight to the component, thereby producing a microcapsule including said component and said coating, wherein said coating reduces the volume of said component by at least 30% relative to the volume of said component prior to coating said component.

2. The method of claim 1, wherein the polyamino acid comprises polylysine.

3. The method of claim 1, wherein the polyamino acid comprises polylysine having a molecular weight of less than 15 kDa.

4. The method of claim 1, wherein said component comprises a living cell encapsulated in a gel matrix which forms said gel particle.

5. The method of claim 4, wherein the living cell is an islet cell.

6. The method of claim 5, wherein said cell is a porcine islet cell.

7. The method of claim 1, wherein the diameter of the microcapsule is less than 4 millimeters.

8. The method of claim 1, wherein the diameter of the gel particle is more than 1 millimeter.

9. The method of claim 1, wherein the diameter of the microcapsule is more than 4 millimeters.

10. The method of claim 1, wherein said living cell is a genetically engineered living cell.

11. The method of claim 1, wherein the polyamino acid comprises polyornithine.

12. A composite microreactor which includes:
    (a) an internal particle which includes:
       (i) a living cell: and
       (ii) an internal particle alginate gel matrix, said living cell being in said matrix;
    (b) an internal particle coating on said internal particle, said coating comprising a polyamino acid of 15,000 daltons or less in molecular weight, said coating reducing the volume of said internal particle by greater than 30% relative to the volume of said internal particle prior to coating said internal particle; and
    (c) a gel super matrix in which the coated internal particle is embedded; the composite microreactor providing a molecular weight cutoff that prevents molecules larger than about 400,000 daltons from coming into contact with said living cell.

13. The composite microreactor of claim 12, wherein the polyamino acid comprises polylysine.

14. The composite microreactor of claim 12, wherein the polyamino acid comprises polylysine having a molecular weight of less than 15 kDa.

15. The composite microreactor of claim 12, wherein said cell is an islet cell.

16. The composite microreactor of claim 12, wherein said cell is a porcine islet cell.

17. The composite microreactor of claim 12, wherein the gel super matrix comprises alginate.

18. The composite microreactor of claim 12, wherein the diameter of the internal particle is between 50 and 700 microns and the diameter of the composite microreactor is between 300 and 1500 microns.

19. The composite microreactor of claim 12, wherein the composite microreactor includes between 2 and 100 internal particles.

20. The composite microreactor of claim 12, wherein the internal particle alginate gel matrix is treated by allowing it to age for between 2 hours and 14 days prior to applying the internal particle coating.

21. The composite microreactor of claim 12, wherein the internal particle coating has a lower molecular weight exclusion number than does the gel super matrix.

22. The composite microreactor of claim 12, wherein the diameter of the composite microreactor is less than 4 millimeters.

23. The composite microreactor of claim 12, wherein the diameter of the internal particle is more than 1 millimeter.

24. The composite microreactor of claim 12, wherein the diameter of the composite microreactor is more than 4 millimeters.

25. The composite microreactor of claim 12, wherein said living cell is a genetically engineered living cell.

26. The composite microreactor of claim 12, wherein said polyamino acid comprises polyornithine.

27. The composite microreactor of claim 12, having a single internal particle.

28. A method of implanting a living donor cell into a recipient comprising:
    providing the composite microreactor of claim 12, which contains the living donor cell; and implanting the composite microreactor into said recipient.

29. The method of claim 28, further comprising testing the recipient for antibodies to the living donor cell.

30. The method of claim 28, wherein no adjunctive immunosuppression is administered to the recipient.

31. A double composite microreactor which includes:
(1) an internal particle which includes:
   (a) a living cell;
   (b) an internal particle alginate gel matrix which contains said living cell; and
   (c) an internal particle coating, which is semipermeable, on the internal particle alinate gel matrix;
(2) a particle which includes:
   (a) at least one internal particle of (1);
   (b) a particle alginate gel matrix in which the internal particle is embedded;
   (c) a particle coating on the particle alginate gel matrix; and
(3) a gel super matrix in which the particle of (2) is embedded, wherein at least one of the coating in (1)c and the coating in (2)c is a volume-reducing coating of polyamino acid of 15,000 daltons or less in molecular weight.

32. The double composite microreactor of claim 31, wherein the internal particle coating (1)c is polylysine.

33. The double composite microreactor of claim 31, wherein the internal particle coating (1)c is polylysine having a molecular weight of less than 15 kDa.

34. The double composite microreactor of claim 31, wherein the particle coating (2)c is polylysine.

35. The double composite microreactor of claim 31, wherein the particle coating (2)c is polylysine having a molecular weight of less than 15 kDa.

36. The double composite microreactor of claim 31, wherein the gel super matrix comprises alginate.

37. The double composite microreactor of claim 31, wherein the diameter of the internal particle is between 50 and 700 microns, the diameter of the particle is between 400 and 800 microns, and the diameter of the double composite microreactor is between 300 and 1500 microns.

38. The double composite microreactor of claim 31, wherein said cell is an islet cell.

39. The double composite microreactor of claim 31, wherein said cell is a porcine islet cell.

40. The double composite microreactor of claim 31, wherein the diameter of the double composite microreactor is less than 4 millimeters.

41. The double composite microreactor of claim 31, wherein the diameter of the internal particle is more than 1 millimeter.

42. The double composite microreactor of claim 31, wherein the diameter of the composite microreactor is more than 4 millimeters.

43. The double composite microreactor of claim 31, wherein said living cell is a genetically engineered cell.

44. The double composite microreactor of claim 31, wherein at least one of said internal particle coating and said particle coating comprises polyornithine.

45. The double composite microreactor of claim 31, having a single internal particle and a single particle.

46. The double composite microreactor of claim 31, wherein the volume-reducing coating reduces the volume of at least one of the internal particle alignate gel matrix and the particle alginate gel matrix by 30% or more relative to the volume prior to coating.

47. A double composite microreactor which includes:
(1) an internal particle which includes:
   (a) a living cell;
   (b) an internal particle gel matrix in which the living cell is embedded;
   (c) an internal particle coating enclosing the internal particle gel matrix;
(2) a particle which includes:
   (a) at least one internal particle of (1);
   (b) a particle gel matrix in which the internal particle is embedded; and
   (c) a particle coating enclosing the particle gel matrix; and
(3) a gel super matrix in which the particle of (2) is embedded, wherein at least one of (i) the thickness of the particle gel matrix 2(b) and (ii) the thickness of the gel super matrix is at least 10 microns.

48. The double composite microreactor of claim 47, having a single internal particle and a single particle.

49. A double composite microreactor which includes:
(1) an internal particle which includes:
   (a) a living cell;
   (b) an internal particle gel matrix containing said living cell; and
   (c) an internal particle coating on the internal particle gel matrix;
(2) a particle which includes:
   (a) at least one internal particle of (1)
   (b) a particle gel matrix in which the internal particle is embedded;
   (c) a particle coating on the particle gel matrix; and
(3) a gel super matrix in which the particle of (2) is embedded, wherein at least one of the internal particle gel matrix, the particle gel matrix and the particle has been treated such that no substantial change in shape or volume occurs when combined respectively with the internal particle coating, the particle coating or the gel super matrix.

50. The double composite microreactor of claim 49, wherein said treatment is by aging for between 2 hours and 14 days.

51. The double composite microreactor of claim 49, wherein at least one of said internal particle gel matrix, internal particle tin particle gel matrix, particle coating or gel super matrix has been treated by aging for between 2 hours and 14 days.

52. The double composite microreactor of claim 49, wherein the internal particle coating (1)c is polylysine.

53. The double composite microreactor of claim 49, wherein the internal particle coating (1)c is polylysine having a molecular weight of less than 15 kDa.

54. The double composite microreactor of claim 49, wherein the particle coating (2)c is polylysine.

55. The double composite microreactor of claim 49, wherein the particle coating (2)c is polylysine having a molecular weight of less than 15 kDa.

56. The double composite microreactor of claim 49, wherein said internal particle gel matrix (1)b comprises alginate.

57. The double composite microreactor of claim 49, wherein said particle gel matrix (2)b comprises alginate.

58. The double composite microreactor of claim 49, wherein the living cell is an islet cell.

59. The double composite microreactor of claim 49, wherein the living cell is a porcine islet cell.

60. The double composite microreactor of claim 49, wherein at least one of the internal particle coating and the particle coating comprises a polyamino acid.

61. The double composite microreactor of claim 49, wherein the diameter of the internal particle is between 50 and 700 microns, the diameter of the particle is between 400 and 800 microns, and the diameter of the double composite microreactor is between 300 and 1500 microns.

62. The double composite microreactor of claim 49, wherein the diameter of the double composite microreactor is less than 4 millimeters.

63. The double composite microreactor of claim 49, wherein the diameter of the internal particle is more than 1 millimeter.

64. The double composite microreactor of claim 49, wherein the diameter of the double composite microreactor is more than 4 millimeters.

65. The double composite microreactor of claim 49, wherein said living cell is a genetically engineered living cell.

66. The double composite microreactor of claim 49, wherein at least one of said internal article coating and said particle coating comprises polyornithine.

67. The double composite microreactor of claim 49, having a single internal particle and a single particle.

68. A double composite microreactor which includes:
   (1) an internal particle which includes:
      (a) a living cell;
      (b) an internal particle gel matrix containing said living cell; and
      (c) an internal particle coating on the internal particle gel matrix;
   (2) a particle which includes:
      (a) at least one internal particle of (1)
      (b) a particle gel matrix in which the internal particle is embedded;
      (c) a particle coating on the particle gel matrix; and
   (3) a gel supermatrix in which the particle of (2) is embedded, wherein the double composite microreactor has one or more of the following properties:
      the microreactor includes a plurality of internal particles;
      the microreactor includes a plurality of particles;
      the thickness of the gel supermatrix is at least 20 microns; or
      the thickness of the particle gel matrix is at least 20 microns.

69. The double composite microreactor of claim 68, wherein the internal particle coating is polylysine.

70. The double composite microreactor of claim 68, wherein the internal particle coating is polylysine having a molecular weight of less than 15 kDa.

71. The double composite microreactor of claim 68, wherein the particle coating is polylysine.

72. The double composite microreactor of claim 68, wherein the particle coating is polylysine having a molecular weight of less than 15 kDa.

73. The double composite microreactor of claim 68, wherein said internal particle gel matrix comprises alginate.

74. The double composite microreactor of claim 68, wherein said particle gel matrix comprises alginate.

75. The double composite microreactor of claim 68, wherein the living cell is an islet cell.

76. The double composite microreactor of claim 68, wherein at least one of the internal particle coating and the particle coating comprises a polyamino acid.

77. The double composite microreactor of claim 68, wherein the diameter of the double composite microreactor is less than 4 millimeters.

78. The double composite microreactor of claim 68, wherein the diameter of the internal particle is more than 1 millimeter.

79. The double composite microreactor of claim 68, wherein the diameter of the double composite microreactor is more than 2 millimeters.

80. The double composite microreactor of claim 68, wherein said living cell is a genetically engineered living cell.

81. The double composite microreactor of claim 68, wherein at least one of said internal particle coating and said particle coating comprises polyomithine.

82. The double composite microreactor of claim 68, having a single internal particle and a single particle.

* * * * *

UNITED STATES PATENT AND TRADEMARK OFFICE
CERTIFICATE OF CORRECTION

PATENT NO.   : 6,126,936
DATED        : October 3, 2000
INVENTOR(S)  : Robert P. Lanza, Willem M. Kühtreiber, William L. Chick It is certified that error appears in the above-identified patent and that said Letters Patent is hereby corrected as shown below:

Title page,
ABSTRACT, after "300 and 1500 microns." first occurrence, delete the remaining text of the ABSTRACT.

Signed and Sealed this

Twenty-ninth Day of January, 2002

*Attest:*

JAMES E. ROGAN
*Attesting Officer*   *Director of the United States Patent and Trademark Office*